US009487593B2

(12) United States Patent
Powell et al.

(10) Patent No.: US 9,487,593 B2

(45) Date of Patent: Nov. 8, 2016

(54) RESPIRATORY SYNCYTIAL VIRUS ANTIGENIC COMPOSITIONS AND METHODS

(75) Inventors: Thomas J. Powell, Madison, CT (US); James Gorham Boyd, Mystic, CT (US)

(73) Assignee: ARTIFICIAL CELL TECHNOLOGIES, INC, New Haven, CT (US)

( * ) Notice: Subject to any disclaimer, the term of this patent is extended or adjusted under 35 U.S.C. 154(b) by 225 days.

(21) Appl. No.: 13/177,671

(22) Filed: Jul. 7, 2011

(65) Prior Publication Data

US 2012/0009254 A1 Jan. 12, 2012

Related U.S. Application Data

(60) Provisional application No. 61/362,029, filed on Jul. 7, 2010, provisional application No. 61/485,669, filed on May 13, 2011.

(51) Int. Cl.

| | |
|---|---|
| ***A61K 9/00*** | (2006.01) |
| ***A61K 39/155*** | (2006.01) |
| ***C07K 17/14*** | (2006.01) |
| ***A61K 47/48*** | (2006.01) |
| ***A61K 39/12*** | (2006.01) |
| *A61K 39/00* | (2006.01) |

(52) U.S. Cl.

CPC ............... *C07K 17/14* (2013.01); *A61K 39/12* (2013.01); *A61K 39/155* (2013.01); *A61K 47/48884* (2013.01); *A61K 2039/543* (2013.01); *A61K 2039/55555* (2013.01); *A61K 2039/60* (2013.01); *A61K 2039/6093* (2013.01); *C12N 2760/18534* (2013.01)

(58) Field of Classification Search

None

See application file for complete search history.

(56) References Cited

U.S. PATENT DOCUMENTS

| | | | | |
|---|---|---|---|---|
| 6,077,511 | A | 6/2000 | Langedijk | |
| 6,113,911 | A | 9/2000 | Binz et al. | |
| 7,309,404 | B2 | 12/2007 | Anazawa et al. | |
| 7,615,530 | B2 | 11/2009 | Haynie | |
| 8,883,717 | B2 * | 11/2014 | Powell | A61K 39/015 514/1.1 |
| 2005/0069950 | A1 | 3/2005 | Haynie | |
| 2008/0025997 | A1 | 1/2008 | Polack et al. | |
| 2008/0131450 | A1 | 6/2008 | Libon et al. | |
| 2008/0171070 | A1 * | 7/2008 | Schaaf et al. | 424/422 |
| 2010/0028448 | A1 | 2/2010 | Haynie | |
| 2011/0177117 | A1 | 7/2011 | Blais et al. | |

FOREIGN PATENT DOCUMENTS

| | | | |
|---|---|---|---|
| WO | 9614416 | A1 | 5/1996 |
| WO | WO 97/46581 | * | 11/1997 |
| WO | 9746581 | A1 | 12/1997 |
| WO | 0258725 | A2 | 1/2002 |
| WO | 0232942 | A2 | 4/2002 |
| WO | 02094858 | A1 | 11/2002 |
| WO | 2005007189 | A1 | 1/2005 |
| WO | WO2006/108226 | * | 10/2006 |
| WO | 2008110627 | A1 | 9/2008 |
| WO | 2008114149 | A2 | 9/2008 |
| WO | 2009079066 | A2 | 6/2009 |
| WO | 2010075491 | A2 | 7/2010 |
| WO | 2011017442 | A2 | 2/2011 |

OTHER PUBLICATIONS

Voegel, J-C., ACS Nano. Nov. 24, 2009; vol. 3(11) pp. 3343-3346.*

Ward et al., J Gen Virol. 2008 vol. 89(Pt 3): pp. 741-750.*

Chong, et al.; "A Paradigm for Peptide Vaccine Delivery Using Viral Epitopes Encapsulated in Degradable Polymer Hydrogel Capsules"; Biomaterials; 30; pp. 5178-5186; (2009).

Ciobanu et al.; "Layersome: Development and Optimization of Stable Liposomes as Drug Delivery System"; International Journal of Pharmaceutics; 344; pp. 154-157; (2007).

International Search Report and Written Opinion; International Application No. PCT/US2011/043136; International Filing Date Jul. 7, 2011; Date of Mailing Oct. 17, 2011; 18 pages.

Look, et al.; "Application of Nanotechnologies for Improved Immune Response Against Infectious Diseases in the Developing World"; Advanced Drug Delivery Reviews; 62; pp. 378-393; (2010).

Mottram, et al.; "Type 1 and 2 Immunity Following Vaccination is Influenced by Nanoparticle Size: Formulation of a Model Vaccine for Respiratory Syncytial Virus"; Molecular Pharmaceutics; 4(1); pp. 73-84; (2007).

Murata, Yoshihiko; "Respiratory Syncytial Virus Vaccine Development"; Clin Lab Med; 29(4); pp. 725-739; (2009).

Su et al.; "Layer-by-Layer Assembled Multilayer Films for Transcutaneous Drug and Vaccine D elivery"; ACS Nano; 3 (11); pp. 3719-3729; (2009); retrieved from the Internet: URL:http://pubs.acs.org/doi/suppl/10.1021/nn900928u/suppl_file/nn900928u_si_001.pdf on Oct. 4, 2011.

Voegel, Jean-Claude; "Multilayered Polyelectrolyte Films: From Active Molecular Delivery to Vaccine Therapy"; ACS Nano; 3(11); pp. 3343-3346; (2009).

Bastien et al.; "Protective Immune Responses Induced by the Immunization of Mice with a Recombinant Bacteriophage Display an Epitope of the Human Respiratory Syncytial Virus"; Virology; 234; pp. 118-122; (1997).

Zhang, et al.; "Vaccination to Induce Antibodies Blocking the CX3C-CX3CR1 Interaction of Respiratory Syncytial Virus G Protein Reduces Pulmonary Inflammation and Virus Replication in Mice"; Journal of Virology; 84(2); pp. 1148-1157; (2010).

(Continued)

*Primary Examiner* — Shanon A Foley

*Assistant Examiner* — Myron Hill

(74) *Attorney, Agent, or Firm* — Cantor Colburn LLP

(57) ABSTRACT

Multilayer films comprise polypeptide epitopes from RSV. The multilayer films are capable of eliciting an immune response in a host upon administration to the host. The multilayer films include at least one designed peptide that includes one or more polypeptide epitopes from RSV. Specifically, the multilayer films include two polypeptide epitopes from RSV, such as an epitope that elicits a specific T-cell response such as a cytotoxic T-cell response, and an epitope that elicits a specific antibody response.

9 Claims, 10 Drawing Sheets

(56) References Cited

OTHER PUBLICATIONS

Anderson, L.J.; "Respiratory Syncytical Virus Vaccine Development"; Semin Immunol; 25(2); pp. 160-171; (2013); Abstract only; 1 page.
Jorquera et al.; "Advances in and the Potential of Vaccines for Respiratory Syncytial Virus"; Expert Rev Respir Med.; 7(4); pp. 411-427; (2013); Abstract only, 1 page.
Shaw et al.; "The path to an RSV Vaccine"; Curr Opin Virol; 3(3); pp. 332-342; (2013); Abstract only; 1 page.
Bukreyev et al.; "The Cysteine-Rich Region and Secreted Form of the Attachment G Glycoprotein in Respiratory Syncytial Virus Enhance the Cytotoxic T Lymphocyte Response Despite Lacking Major Histocompatibility Complex Class I-Restricted Epitopes", Journal of Virology, 80, pp. 5854-5861 (2006).
EP Search Report; Appplication No. 11 731 610.9-1403; dated Aug. 15, 2014; 6 pages.
Fan et al.; "Co-immunization of BALA/c Mice with Recombinant Immunogens Containing G Protein Fragment and Chimeric CCTL Epitope of Respiratory Sycytial Virus Induces Enhanced Cellular Immunity and High Level of Antibody Response"; Vaccine, 23(35); pp. 4453-4461; (2005).
Zeng et al.; "Induction of Balanced Immunity in BALB/c Mice by Vaccination with a Recombinant Fusion Protein Containing a Respiratory Syncytial Virus G Protein Fragment and a CTL Epitope"; Vaccine, 24(7) pp. 941-947 (2006).
Bem et al.; "Animal Models of Human Respiratory Syncytial Virus Disease"; Am. J. Physiol Lung Cell Mol Physiol; 301; pp. L148-L156; (2011).
Lee et al.; "Targeting CD137 Enhances Vaccine-Elicited Anti-Respiratory Syncytial Virus CD8+ T Cell Responses in Aged Mice"; The Journal of Immunology; 192; pp. 293-299; (2014).
Taylor et al.; "Respiratory Syncytial Virus Infection in Mice"; Infection and Immunity; 43; pp. 649-655; (1984).
RU Application No. 2013101972, Office Action of Oct. 28, 2015, English Translation, three pages.

* cited by examiner

RESPIRATORY SYNCYTIAL VIRUS ANTIGENIC COMPOSITIONS AND METHODS

CROSS-REFERENCE TO RELATED APPLICATIONS

The present application is a nonprovisional of U.S. Provisional Application Nos. 61/485,669, filed on May 13, 2011, and 61/362,029 filed on Jul. 7, 2010, both of which are incorporated herein in their entirety.

FIELD OF THE DISCLOSURE

The present disclosure relates to compositions and methods for the prevention of infection by respiratory syncytial virus, specifically multilayer film compositions containing antigenic epitopes.

BACKGROUND

Respiratory syncytial virus (RSV) is the most important cause of serious lower respiratory tract disease in infants and young children worldwide, and is also a threat to elderly and immune compromised patients. In the United States, RSV infections result in up to 126,000 infant hospitalizations and up to 60,000 elderly adult hospitalizations per year. Since natural RSV infection does not induce durable long-term immunity, patients are susceptible to re-infection with the same and different strains of virus throughout life. RSV is associated with secondary infections such as otitis media, and it may predispose young children for asthma-related illness later in life.

After more than 40 years of effort, there is no safe and effective RSV vaccine. The earliest attempts to develop a formalin-inactivated alum-precipitated RSV (FI-RSV) vaccine in the 1960's actually appeared to predispose vaccinated children to more severe disease and even death upon subsequent natural infection. The exact mechanism of this response has not been fully characterized, but it appears to be dependent on a skewing of the immune response toward an inflammatory Th2-dominant phenotype characterized by inappropriate activation of cytokine and chemokine pathways.

Given the economic impact of RSV disease, estimated at nearly $700 million per year in the US in 2004, and the life-threatening complications that can result from RSV infection in infants, elderly, and immunocompromised patients, development of safe and effective RSV vaccines is a high priority.

There is a need for improved antigenic compositions suitable for stimulating an immune response to RSV.

SUMMARY

In one embodiment, a composition comprises a first polypeptide epitope from RSV and a second polypeptide epitope from RSV, wherein the first and second polypeptide epitopes are covalently linked to one or more polyelectrolytes, wherein the one or more polyelectrolytes are in one or more multilayer films, wherein the one or more multilayer films each comprises two or more layers of polyelectrolytes, wherein adjacent layers comprise oppositely charged polyelectrolytes, and wherein the polyelectrolyte comprises a polycationic material or a polyanionic material having a molecular weight of greater than 1,000 and at least 5 charges per molecule, and wherein the first polypeptide epitope from RSV and the second polypeptide epitope from RSV are present in the same or different multilayer film.

In another embodiment, a composition comprises a first polypeptide epitope from RSV and a second polypeptide epitope from RSV, wherein the first and second polypeptide epitopes are in the form of one or more multilayer films, wherein the one or more multilayer films each comprises two or more layers of polyelectrolytes, wherein adjacent layers comprise oppositely charged polyelectrolytes, and wherein at least one polyelectrolyte of the multilayer film comprises a designed polypeptide, wherein the designed polypeptide has sufficient charge for stable binding to an oppositely charged surface, and wherein the designed polypeptide comprises the first polypeptide epitope from RSV, the second polypeptide epitope from RSV, or both, wherein a polyelectrolyte that is not a designed polypeptide comprises a polycationic material or a polyanionic material having a molecular weight of greater than 1,000 and at least 5 charges per molecule, and wherein the first polypeptide epitope from RSV and the second polypeptide epitope from RSV are present in the same or different multilayer film.

A composition comprises an RSV-G polypeptide epitope covalently linked to one or more polyelectrolytes, wherein the one or more polyelectrolytes are in one or more multilayer films, wherein the one or more multilayer films each comprises two or more layers of polyelectrolytes, wherein adjacent layers comprise oppositely charged polyelectrolytes, and wherein the polyelectrolye comprises a polycationic material or a polyanionic material having a molecular weight of greater than 1,000 and at least 5 charges per molecule.

BRIEF DESCRIPTION OF THE DRAWINGS

FIG. 11: Immunogenicity of multivalent RSV nanoparticle cocktail vaccine. BALB/c mice (5/group, 5-6 weeks old) were immunized on days 0 and 21. T-cell responses to RSV-M2: Spleen cells were harvested on day 28 and restimulated with RSV-M2 (ACT-2031; SEQ ID NO: 12) peptide in IFNγ or IL-4 ELISPOT plates. The data depict the mean±SD of 5 mice per group.

Figure 1:
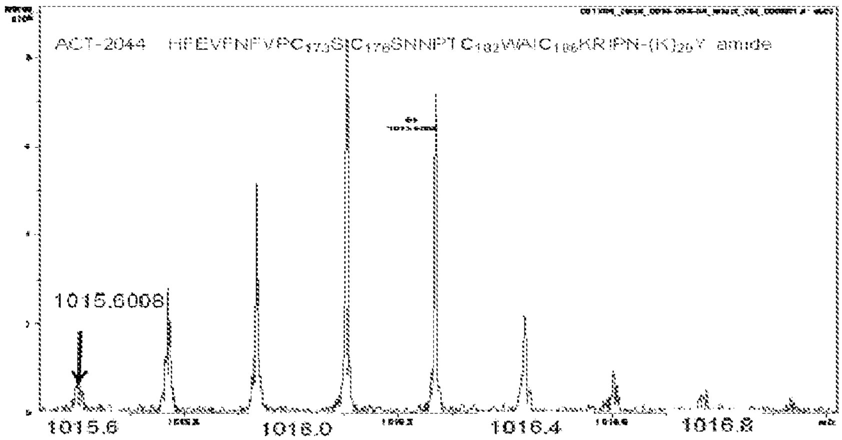
FIG. 1: Expanded FT-ICR mass spectrum for the $MH_6^{+6}$ charge state of intact ACT-2044 (SEQ ID NO: 8). Expected monoisotopic m/z for fully oxidized peptide=1015.43, found=1015.6008. This result is fully consistent with two intramolecular disulfides in ACT-2044.

The above-described and other features will be appreciated and understood by those skilled in the art from the following detailed description, drawings, and appended claims.

DETAILED DESCRIPTION

Disclosed herein are multilayer films comprising polypeptide epitopes from RSV, wherein the multilayer films are capable of eliciting an immune response in a host upon administration to the host. In one embodiment, the multilayer films comprise two polypeptide epitopes from RSV, specifically an epitope that elicits a specific T-cell response such as a cytotoxic T-cell response, and an epitope that elicits a specific antibody response. In this embodiment, it has been unexpectedly shown by the inventors herein that by combining an epitope that elicits a specific T-cell response and an epitope that elicits a specific antibody response, the immune potency measured as the T-cell response is unexpectedly improved compared to administration of only one component. Specifically, a combination of RSV-G (specific antibody response) and RSV-M2 (specific T-cell response) epitopes in the form of one or more multilayer films elicit a substantially improved T-cell response compared to a multilayer film containing the RSV-M2 epitope alone.

Specifically, the multilayer films comprise alternating layers of oppositely charged polyelectrolytes in which one polyelectrolyte layer comprises a polyelectrolyte having covalently attached thereto at least one polypeptide epitope from RSV. First and second RSV polypeptide epitopes can be attached to the same or different polyelectrolytes, and/or can be present in the same or different multilayer film. In one embodiment, first and second RSV polypeptide epitopes are covalently attached to the same polyelectrolyte and thus are in the same multilayer film. In another embodiment, first and second RSV polypeptide epitopes are covalently attached to different polyelectrolytes, but are layered within the same multilayer film. In yet another embodiment, first and second RSV polypeptide are covalently attached to different polyelectrolytes, but are layered in different multilayer films which are subsequently mixed prior to administration.

In one embodiment, the multilayer films comprise alternating layers of oppositely charged polyelectrolytes in which one polyelectrolyte layer is a designed polypeptide comprising at least one polypeptide epitope from RSV. The first and second RSV polypeptide epitopes can be present in the same or different designed polypeptide, and/or can be present in the same or different multilayer film. In one embodiment, the first and second RSV polypeptide epitopes are present in the same designed polypeptide and thus are in the same multilayer film. In another embodiment, the first and second RSV polypeptide are present in different designed polypeptides, but are layered within the same multilayer film. In yet another embodiment, the first and second RSV polypeptide are present in different designed polypeptides, but are layered in different multilayer films which are subsequently mixed prior to administration.

In one embodiment, the RSV polypeptide epitopes are from the RSV-G protein. The RSV-G (attachment) protein has been associated with many aberrations including altered CC and CXC chemokine mRNA expression and Th2 cytokine responses which appear to support inappropriate immune outcomes and enhanced disease. The central cysteine-rich conserved region of the RSV-G protein contains a CX3C chemokine motif at amino acid positions 182-186 which binds to CX3CR1, the fractalkine (CX3CL1) receptor. CX3CL1 mimicry by RSV-G has been shown to facilitate RSV infection and interfere with normal adaptive immune responses to the virus. Active immunization with peptides spanning the RSV-G CX3C motif protects mice from RSV infection and pulmonary inflammation. Thus far, these RSV-G peptides have not been developed into a safe and effective vaccine.

In another embodiment, the RSV polypeptide epitopes are from the RSV-F or RSV-M2 protein. In addition to the RSV-G protein, the RSV-F (fusion) and RSV-M2 (matrix) protein are possible vaccine candidates. Attempts to develop monovalent RSV vaccines containing only one of the major antigenic determinants have been hampered by incomplete protection from infection and inflammatory disease, suggesting that a multivalent approach might be more successful. Indeed, immunization of mice with multivalent vaccines that elicited both antibody and CD8+ T-cell responses resulted in a decrease in Th2 and an increase in Th1/CD8 responses that correlated with greater protection from virus infection and less inflammatory lung pathology. These results suggest that the ideal RSV vaccine design would include epitopes from two or more viral proteins and would elicit both antibodies and CD8+ T-cells secreting IFNγ.

In another embodiment, a multilayer film comprises a polypeptide epitope from RSV, wherein the polypeptide epitope is from the RSV-G protein (specific antibody response). It was unexpectedly found that mice immunized with nanoparticles containing an RSV-G CX3C epitope were protected from challenge with live RSV. Interestingly, an RSV-M2 epitope did not provide protection from live RSV challenge and a combination RSV-G and RSV-M2 vaccine did not provide improved protection compared to RSV-G alone. Without being held to theory, it is believed that the high concentration of nanoparticles used in these experiments may have masked the potential benefits of the combination nanoparticles.

In one embodiment, the multilayer film is deposited on a core particle, such as a $CaCO_3$ nanoparticle, a latex particle, or an iron particle. Particle sizes on the order of 5 nanometers (nm) to 50 micrometers (um) in diameter are particularly useful. Particles made of other materials can also be used as cores provided that they are biocompatible, have controllable size distribution, and have sufficient surface charge (either positive or negative) to bind polyelectrolyte peptides. Examples include nanoparticles and microparticles made of materials such as polylactic acid (PLA), polylactic acid glycolic acid copolymer (PLGA), polyethylene glycol (PEG), chitosan, haluronic acid, gelatin, or combinations thereof. Core particles could also be made of materials that are believed to be inappropriate for human use provided that they can be dissolved and separated from the multilayer film following film fabrication. Examples of the template core substances include organic polymers such as latex or inorganic materials such as silica.

Polyelectrolyte multilayer films are thin films (e.g., a few nanometers to micrometers thick) composed of alternating layers of oppositely charged polyelectrolytes. Such films can be formed by layer-by-layer assembly on a suitable substrate. In electrostatic layer-by-layer self-assembly ("ELBL"), the physical basis of association of polyelectrolytes is electrostatic attraction. Film buildup is possible because the sign of the surface charge density of the film reverses on deposition of successive layers. The generality and relative simplicity of the ELBL film process permits the deposition of many different types of polyelectrolyte onto many different types of surface. Polypeptide multilayer films are a subset of polyelectrolyte multilayer films, comprising at least one layer comprising a charged polypeptide, herein referred to as a designed polypeptide. A key advantage of polypeptide multilayer films over films made from other polymers is their biocompatibility. ELBL films can also be used for encapsulation. Applications of polypeptide films and microcapsules include, for example, nano-reactors, biosensors, artificial cells, and drug delivery vehicles.

The term "polyelectrolyte" includes polycationic and polyanionic materials having a molecular weight of greater than 1,000 and at least 5 charges per molecule. Suitable polycationic materials include, for example, polypeptides and polyamines. Polyamines include, for example, a polypeptide such as poly-L-lysine (PLL) or poly-L-ornithine, polyvinyl amine, poly(aminostyrene), poly(aminoacrylate), poly(N-methyl aminoacrylate), poly (N-ethylaminoacrylate), poly(N,N-dimethyl aminoacrylate), poly(N,N-diethylaminoacrylate), poly(aminomethacrylate), poly(N-methyl amino-methacrylate), poly(N-ethyl aminomethacrylate), poly(N,N-dimethyl aminomethacrylate), poly(N,N-diethyl aminomethacrylate), poly(ethyleneimine), poly(diallyl dimethylammonium chloride), poly(N,N,N-trimethylaminoacrylate chloride), poly(methyacrylamidopropyltrimethyl ammonium chloride), chitosan and combinations comprising one or more of the foregoing polycationic materials. Suitable polyanionic materials include, for example, a polypeptide such as poly-L-glutamic acid (PGA) and poly-L-aspartic acid, a nucleic acid such as DNA and RNA, alginate, carrageenan, furcellaran, pectin, xanthan, hyaluronic acid, heparin, heparan sulfate, chondroitin sulfate, dermatan sulfate, dextran sulfate, poly(meth)acrylic acid, oxidized cellulose, carboxymethyl cellulose, acidic polysaccharides, and croscarmelose, synthetic polymers and copolymers containing pendant carboxyl groups, and combinations comprising one or more of the foregoing polyanionic materials. In one embodiment, the RSV epitope and the polyelectrolyte have the same sign of charge.

In one embodiment, one or more polyelectrolye layers of the film, optionally including the polyelectrolyte comprising the RSV epitope, is a designed polypeptide. In one embodiment, the design principles for polypeptides suitable for electrostatic layer-by-layer deposition are elucidated in U.S. Patent Publication No. 2005/0069950, incorporated herein by reference for its teaching of polypeptide multilayer films. Briefly, the primary design concerns are the length and charge of the polypeptide. Electrostatics is the most important design concern because it is the basis of ELBL. Without suitable charge properties, a polypeptide may not be substantially soluble in aqueous solution at pH 4 to 10 and cannot readily be used for the fabrication of a multilayer film by ELBL. Other design concerns include the physical structure of the polypeptides, the physical stability of the films formed from the polypeptides, and the biocompatibility and bioactivity of the films and the constituent polypeptides.

A designed polypeptide means a polypeptide that has sufficient charge for stable binding to an oppositely charged surface, that is, a polypeptide that can be deposited into a layer of a multilayer film wherein the driving force for film formation is electrostatics. A short stable film is a film that once formed, retains more than half its components after incubation at in PBS at 37° C. for 24 hours. In specific embodiments, a designed polypeptide is at least 15 amino acids in length and the magnitude of the net charge per residue of the polypeptide is greater than or equal to 0.1, 0.2, 0.3, 0.4 or 0.5 at pH 7.0. Positively-charged (basic) naturally-occurring amino acids at pH 7.0 are arginine (Arg), histidine (His), ornithine (Orn), and lysine (Lys). Negatively-charged (acidic) naturally-occurring amino acid residues at pH 7.0 are glutamic acid (Glu) and aspartic acid (Asp). A mixture of amino acid residues of opposite charge can be employed so long as the overall net ratio of charge meets the specified criteria. In one embodiment, a designed polypeptide is not a homopolymer. In another embodiment, a designed polypeptide is unbranched.

One design concern is control of the stability of polypeptide ELBL films. Ionic bonds, hydrogen bonds, van der Waals interactions, and hydrophobic interactions contribute to the stability of multilayer films. In addition, covalent disulfide bonds formed between sulfhydryl-containing amino acids in the polypeptides within the same layer or in adjacent layers can increase structural strength. Sulfydryl-containing amino acids include cysteine and homocysteine and these residues can be readily incorporated into synthetic designed peptides. In addition sulfhydryl groups can be incorporated into polyelectrolyte homopolymers such as poly-L-lysine or poly-L-glutamic acid by methods well described in the literature. Sulfhydryl-containing amino acids can be used to “lock” (bond together) and “unlock” layers of a multilayer polypeptide film by a change in oxidation potential. Also, the incorporation of a sulfhydryl-containing amino acid in a designed polypeptide enables the use of relatively short peptides in thin film fabrication, by virtue of intermolecular disulfide bond formation.

In one embodiment, the designed sulfhydryl-containing polypeptides, whether synthesized chemically or produced in a host organism, are assembled by ELBL in the presence of a reducing agent to prevent premature disulfide bond formation. Following film assembly, the reducing agent is removed and an oxidizing agent is added. In the presence of the oxidizing agent disulfide bonds form between sulfhydryls groups, thereby “locking” together the polypeptides within layers and between layers where thiol groups are present. Suitable reducing agents include dithiothreitol (DTT), 2-mercaptoethanol (BME), reduced glutathione, tris (2-carboxyethyl)phosphine hydrochloride (TCEP), and combinations of more than one of these chemicals. Suitable oxidizing agents include oxidized glutathione, tert-butylhydroperoxide (t-BHP), thimerosal, diamide, 5,5'-dithio-bis-(2-nitro-benzoic acid) (DTNB), 4,4'-dithiodipyridine, sodium bromate, hydrogen peroxide, sodium tetrathionate, porphyrindin, sodium orthoiodosobenzoate, and combinations of more than one of these chemicals.

As an alternative to disulfide bonds, chemistries that produce other covalent bonds can be used to stabilize ELBL films. For films comprised of polypeptides, chemistries that produce amide bonds are particularly useful. In the presence of appropriate coupling reagents, acidic amino acids (those with side chains containing carboxylic acid groups such as aspartic acid and glutamic acid) will react with amino acids whose side chains contain amine groups (such as lysine and ornithine) to form amide bonds. Amide bonds are more stable than disulfide bonds under biological conditions and amide bonds will not undergo exchange reactions. Many reagents can be used to activate polypeptide side chains for amide bonding. Carbodiimide reagents, such as the water soluble 1-ethyl-3-(3-dimethylaminopropyl) carbodiimide (EDC) will react with aspartic acid or glutamic acid at slightly acidic pH, forming an intermediate product that will react irreversibly with an amine to produce an amide bond. Additives such as N-hydroxysuccinimide are often added to the reaction to accelerate the rate and efficiency of amide formation. After the reaction the soluble reagents are removed from the nanoparticles or microparticles by centrifugation and aspiration. Examples of other coupling reagents include diisopropylcarbodiimide, HBTU, HATU, HCTU, TBTU, and PyBOP. Examples of other additives include sulfo-N-hydroxysuccinimide, 1-hydroxbenzotriazole, and 1-hydroxy-7-aza-benzotriazole. The extent of amide cross linking can be controlled by modulating the stoichiometry of the coupling reagents, the time of reaction, or the temperature of the reaction, and can be monitored by techniques such as Fourier transform-infrared spectroscopy (FT-IR).

Covalently cross-linked ELBL films have desirable properties such as increased stability. Greater stability allows for more stringent conditions to be used during nanoparticle, microparticle, nanocapsule, or microcapsule fabrication. Examples of stringent conditions include high temperatures, low temperatures, cryogenic temperatures, high centrifugation speeds, high salt buffers, high pH buffers, low pH buffers, filtration, and long term storage.

A method of making a polyelectrolyte multilayer film comprises depositing a plurality of layers of oppositely charged chemical species on a substrate. In one embodiment, at least one layer comprises a designed polypeptide. Successively deposited polyelectrolytes will have opposite net charges. In one embodiment, deposition of a polyelectrolyte comprises exposing the substrate to an aqueous solution comprising a polyelectrolyte at a pH at which it has a suitable net charge for ELBL. In other embodiments, the deposition of a polyelectrolyte on the substrate is achieved by sequential spraying of solutions of oppositely charged polypeptides. In yet other embodiments, deposition on the substrate is by simultaneous spraying of solutions of oppositely charged polyelectrolytes.

In the ELBL method of forming a multilayer film, the opposing charges of the adjacent layers provide the driving force for assembly. It is not critical that polyelectrolytes in opposing layers have the same net linear charge density, only that opposing layers have opposite charges. One standard film assembly procedure by deposition includes forming aqueous solutions of the polyions at a pH at which they are ionized (i.e., pH 4-10), providing a substrate bearing a surface charge, and alternating immersion of the substrate into the charged polyelectrolyte solutions. The substrate is optionally washed in between deposition of alternating layer.

The concentration of polyelectrolyte suitable for deposition of the polyelectrolyte can readily be determined by one of ordinary skill in the art. An exemplary concentration is 0.1 to 10 mg/mL. For typical non-polypeptide polyelectrolytes such as poly(acrylic acid) and poly(allylamine hydrochloride), typical layer thicknesses are about 3 to about 5 Å, depending on the ionic strength of solution. Short polyelectrolytes typically form thinner layers than long polyelectrolytes. Regarding film thickness, polyelectrolyte film thickness depends on humidity as well as the number of layers and composition of the film. For example, PLL/PGA films 50 nm thick shrink to 1.6 nm upon drying with nitrogen. In general, films of 1 nm to 100 nm or more in thickness can be formed depending on the hydration state of the film and the molecular weight of the polyelectrolytes employed in the assembly.

In addition, the number of layers required to form a stable polyelectrolyte multilayer film will depend on the polyelectrolytes in the film. For films comprising only low molecular weight polypeptide layers, a film will typically have 4 or more bilayers of oppositely charged polypeptides. For films comprising high molecular weight polyelectrolytes such as poly(acrylic acid) and poly(allylamine hydrochloride), films comprising a single bilayer of oppositely charged polyelectrolyte can be stable. Studies have shown that polyelectrolyte films are dynamic. The polyelectrolytes contained within a film can migrate between layers and can exchange with soluble polyelectrolytes of like charge when suspended in a polyelectrolyte solution. Moreover polyelectrolyte films can disassemble or dissolve in response to a change in environment such as temperature, pH, ionic strength, or oxidation potential of the suspension buffer. Thus some polyelectrolytes and particularly peptide polyelectrolytes exhibit transient stability. The stability of peptide polyelectrolyte films can be monitored by suspending the films in a suitable buffer under controlled conditions for a fixed period of time, and then measuring the amounts of the peptides within the film with a suitable assay such as amino acid analysis, HPLC assay, or fluorescence assay. Peptide polyelectrolyte films are most stable under conditions that are relevant to their storage and usage as vaccines, for example in neutral buffers and at ambient temperatures such as 4° C. to 37° C. Under these conditions stable peptide polyelectrolyte films will retain most of their component peptides for at least 24 hours and often up to 14 days and beyond.

In one embodiment, a designed polypeptide comprises one or more surface adsorption regions covalently linked to one or more RSV epitopes, wherein the designed polypeptide and the one or more surface adsorption regions have the same sign of charge, that is, are both positively or both negatively charged overall. As used herein, a surface adsorption region is a charged region of a designed polypeptide that advantageously provides sufficient charge so that a peptide containing an epitope from RSV, for example, can be deposited into a multilayer film. In one embodiment, the one or more surface adsorption regions and the one or more RSV epitopes have the same net polarity. In another embodiment, the solubility of the designed polypeptide at pH 4 to 10 is greater than or equal to about 0.1 mg/mL. In another embodiment, the solubility of the designed polypeptide at pH 4 to 10 is greater than or equal to about 1 mg/mL. The solubility is a practical limitation to facilitate deposition of the polypeptides from aqueous solution. A practical upper limit on the degree of polymerization of an antigenic polypeptide is about 1,000 residues. It is conceivable, however, that longer composite polypeptides could be realized by an appropriate method of synthesis.

In one embodiment, a designed polypeptide comprises a single antigenic RSV epitope flanked by two surface adsorption regions, an N-terminal surface adsorption region and a C-terminal surface adsorption region. In another embodiment, a designed polypeptide comprises a single antigenic RSV epitope flanked by one surface adsorption region linked to the N-terminus of the RSV epitope. In another embodiment, a designed polypeptide comprises a single antigenic RSV epitope flanked by one surface adsorption regions linked to the C-terminus of the RSV epitope.

Each of the independent regions (e.g., RSV epitopes and surface adsorption regions) of the designed polypeptide can be synthesized separately by solution phase peptide synthesis, solid phase peptide synthesis, or genetic engineering of a suitable host organism. Solution phase peptide synthesis is the method used for production of most of the approved peptide pharmaceuticals on the market today. A combination of solution phase and solid phase methods can be used to synthesize relatively long peptides and even small proteins. Peptide synthesis companies have the expertise and experience to synthesize difficult peptides on a fee-for-service basis. The syntheses are performed under good manufacturing practices (GMP) conditions and at a scale suitable for clinical trials and commercial drug launch.

Alternatively, the various independent regions can be synthesized together as a single polypeptide chain by solution-phase peptide synthesis, solid phase peptide synthesis or genetic engineering of a suitable host organism. The choice of approach in any particular case will be a matter of convenience or economics.

If the various RSV epitopes and surface adsorption regions are synthesized separately, once purified, for example, by ion exchange chromatography or by high performance liquid chromatography, they are joined by peptide bond synthesis. That is, the N-terminus of the surface adsorption region and the C-terminus of the RSV epitope are covalently joined to produce the designed polypeptide. Alternatively, the C-terminus of the surface adsorption region and the N-terminus of the RSV epitope are covalently joined to produce the designed polypeptide. The individual fragments can be synthesized by solid phase methods and obtained as fully protected, fully unprotected, or partially protected segments. The segments can be covalently joined in a solution phase reaction or solid phase reaction. If one polypeptide fragment contains a cysteine as its N-terminal residue and the other polypeptide fragment contains a thioester or a thioester precursor at its C-terminal residue the two fragments will couple spontaneously in solution by a specific reaction commonly known (to those skilled in the art) as Native Ligation. Native Ligation is a particularly attractive option for designed peptide synthesis because it can be performed with fully deprotected or partially protected peptide fragments in aqueous solution and at dilute concentrations.

In one embodiment, the RSV epitopes and/or surface adsorption regions are joined by peptidic or non-peptidic linkages as described in U.S. Pat. No. 7,723,294, incorporated herein by reference for its teaching of the use of non-peptidic linkages to join segments of polypeptides for use in multilayer films. Suitable non-peptidic linkers include, for example, alkyl linkers such as $—NH—(CH_2)_s—C(O)—$, wherein s=2-20. Alkyl linkers are optionally substituted by a non-sterically hindering group such as lower alkyl (e.g., $C_1$-$C_6$), lower acyl, halogen (e.g., Cl, Br), CN, $NH_2$, phenyl, and the like. Another exemplary non-peptidic linker is a polyethylene glycol linker such as $—NH—(CH_2—CH_2—O)_n—C(O)—$ wherein n is such that the linker has a molecular weight of 100 to 5000 Da, specifically 100 to 500 Da. Many of the linkers described herein are available from commercial vendors in a form suitable for use in solid phase peptide synthesis.

In one embodiment, one or more of the polypeptide epitopes from RSV is covalently attached to one or more of the polyelectrolyes, such as a polypeptide or other polyelectrolyte, through covalent bonds. Examples of suitable covalent bonds include amides, esters, ethers, thioethers, and disulfides. One skilled in the art can take advantage of a range of functional groups found within the epitope peptide to engineer a bond to a suitable electrolyte. For instance, a carboxylic acid in the epitope peptide can be found either at the C-terminal or on the side chain of amino acids aspartic acid or glutamic acid. Carboxylic acids can be activated with suitable peptide coupling reagents such as 1-ethyl-3-(3-dimethylaminopropyl) carbodiimide (EDC) for reaction with primary or secondary amines that are found in peptide polyelectrolytes such as poly-L-lysine. The resulting amide bond is stable under ambient conditions. Conversely, the acid groups in a peptide polyelectrolyte can be activated with EDC for reaction with amine groups in the epitope peptide. Useful amine groups can be found at the epitope peptide's N-terminal or on the side chain of lysine residues.

Epitope peptides can also be attached to polyelectrolytes via disulfide bonds. Polyelectrolytes such as PGA or PLL can be chemically modified so that a fraction of their side chains contain sulfhydryl groups. In the presence of a suitable oxidant, those sulfydryls will react with the sulfhydryl group of a cysteine residue contained within the epitope peptide. The cysteine can either be a native cysteine from the protein sequence of a pathogen such as RSV or it can be a non-native cysteine that was intentionally incorporated into the epitope during peptide synthesis. Suitable oxidants include DTNB, 2,2'-dithiopyridine, hydrogen peroxide, cystine, and oxidized glutathione. The attachment of epitope peptides to polyelectrolytes via disulfide bonds is particularly useful. The disulfides are stable under normal conditions of film fabrication and storage but are readily cleaved by reducing agents found naturally in cells, which frees up the epitope peptide for immune processing.

Epitope peptides can also be attached to polyelectrolytes via thioether bonds. Synthetic epitope peptides can be synthesized with appropriate electrophiles such as haloacetyl groups which react specifically with sulfhydryls. For instance, an epitope peptide containing a chloroacetyl at its N-terminal will form a stable bond to sulfhydryl bearing polyelectrolytes such as PGA-SH described above.

Epitope peptides can also be attached covalently to polyelectrolytes through bifunctional linker molecules. Bifunctional linkers usually contain two electrophilic groups that can react with nucleophiles present on either the epitope peptide or the polyelectrolyte molecule. Two classes of linker molecules are sold commercially, homobifunctional linkers and heterobifunctional linkers. Homobifunctional linkers contain two copies of an electrophilic group joined by a nonreactive spacer. Often the electophiles are active esters, such as N-hydroxysuccinimide (NHS) esters or sulfo-N-hyrdoxysuccinimide esters (sulfo NHS) which react with nucleophilic amines. Examples of homobifunctional NHS esters include bis(sulfosuccinimidyl) suberate, disuccinimidyl glutarate, dithiobis(succinimidyl) propionate, disuccinimidyl suberate, disuccinimidyl tartrate. Sometimes the electophiles are aldehyde groups that form imides with nucleophilic amines on the epitope and polyelectrolyte molecules. The imide bonds are transiently stable but can be converted to stable structures with reducing agents such as sodium borohydride or catalytic hydrogenation. The most commonly used homobifunctional aldehyde linker is glutaraldehyde.

Other commonly used homobifunctional linkers contain electrophiles that react specifically with nucleophilic thiols, which can be used to link cysteine containing epitope peptides to sulfhydryl containing polyelectrolytes as described above. Examples of sulfhydryl specific homobifunctional linkers include 1,4-bismaleimidobutane, 1,4 bismaleimidyl-2,3-dihydroxybutane,vbismaleimidohexane, bis-maleimidoethane, 1,4-di-[3'-(2'-pyridyldithio)-propionamido]butane, dithio-bismaleimidoethane, 1,6-hexane-bis-vinyl sulfone.

Members of the heterobifunctional class of cross linking reagents contain two different reactivity groups, often but not always electrophiles, which react specifically with different functional groups in substrate molecules. Particularly useful are linkers that contain one electrophilic group that is specific for a sulfhydryl and another electrophile that is specific for an amine. Examples of these reagents include N-sulfosuccinimidyl[4-iodoacetyl]aminobenzoate, N-succinimidyl[4-iodoacetyl]aminobenzoate, succinimidyl 3-[bromoacetamido]propionate, N-succinimidyl iodoacetate, sulfosuccinimidyl 4-[N-maleimidomethyl]cyclohexane-1-carboxylate, succinimidyl 4-[N-maleimidomethyl]cyclohexane-1-carboxylate, ([N-e-maleimidocaproyloxy]sulfosuccinimide ester, m-maleimidobenzoyl-N-hydroxysulfosuccinimide ester, N-succinimidyl 3-(2-pyridyldithio)-propionate, succinimidyl 6-(3-[2-pyridyldithio]-propionamido)hexanoate, 4-succinimidyloxycarbonyl-methyl-a-[2-pyridyldithio]toluene.

The wide range of functionality that is normally present in both epitope peptides and polyelectrolytes or which can easily be installed in either molecule allows one to chose a linking strategy that best fits the substrates of interest. A likely example is the linking of a cysteine containing epitope peptide to PLL.

The polypeptide segments can be joined in a variety of ways, depending upon the chemistry of the non-peptidic linker. For example, the N-terminus of the first polypeptide segment is joined to the C-terminus of the second polypeptide segment; the N-terminus of the first polypeptide segment is joined to the N-terminus of the second polypeptide segment; the C-terminus of the first polypeptide segment is joined to the C-terminus of the second polypeptide segment; the C-terminus of the first polypeptide segment is joined to the N-terminus of the second polypeptide segment; the C-terminus or the N-terminus of the first polypeptide segment is joined to a pendant side chain of the second polypeptide segment; or the C-terminus or the N-terminus of the second polypeptide segment is joined to a pendant side chain of the first polypeptide segment. Regardless of the point of attachment, however, the first and second segments are covalently joined by a non-peptidic linker.

In one embodiment, a designed polypeptide is a unique combination of covalently attached one or more surface adsorption region(s) and one or more RSV epitope(s). There is no particular limitation on the length of the RSV epitopes, which can be linear epitopes or conformational epitopes. Epitopes can comprise anywhere from about three amino acid resides up to several hundred amino acid residues for complex conformational epitopes.

In one embodiment, a designed polypeptide comprises one RSV epitope and one surface adsorption region. In another embodiment, a designed polypeptide comprises one RSV epitope and two surface adsorption regions, one attached to the N-terminus of the RSV epitope and one attached to the C-terminus of the RSV epitope. The purpose of the surface adsorption region(s) is to enable adsorption of the polypeptide onto an oppositely charged surface in order to build a multilayer film.

The number of surface adsorption regions in a designed polypeptide relative to the number and/or length of the RSV epitopes is related to the solubility requirement. For example, if the RSV epitope is a short amino acid sequence of, for example, three amino acid residues, only one surface adsorption region of at least eight amino acid residues will be required to adsorb the designed polypeptide onto a suitably charged surface. If, by contrast, the RSV epitope is a soluble folded structural domain of a protein comprising, for example, 120 amino acid residues, two surface adsorption regions may be required to impart enough charge for the designed polypeptide to be water soluble and suitable for adsorption. The surface adsorption regions could be contiguous and located at the N-terminus of the domain, contiguous and located at the C-terminus of the domain, or noncontiguous with one at the N-terminus and one at the C-terminus Additionally, an RSV epitope may contain a charged segment (either negatively charged or positively charged) within its native sequence that can serve as a surface adsorption region.

A polypeptide or antigen may contain one or more distinct antigenic determinants. An antigenic determinant may refer to an immunogenic portion of a multichain protein.

Methods and techniques for determining the location and composition of an antigenic determinant or epitope for a specific antibody are well known in the art. These techniques can be used to identify and/or characterize epitopes for use as RSV epitopes. In one embodiment, mapping/characterization methods of an epitope for an antigen specific antibody can be determined by epitope "foot-printing" using chemical modification of the exposed amines/carboxyls in the antigenic protein. One example of such a foot-printing technique is the use of HXMS (hydrogen-deuterium exchange detected by mass spectrometry) wherein a hydrogen/deuterium exchange of receptor and ligand protein amide protons, binding, and back exchange occurs, wherein the backbone amide groups participating in protein binding are protected from back exchange and therefore will remain deuterated. Relevant regions may be identified at this point by peptic proteolysis, fast microbore high-performance liquid chromatography separation, and/or electrospray ionization mass spectrometry.

In another embodiment, a suitable epitope identification technique is nuclear magnetic resonance epitope mapping (NMR), where typically the position of the signals in two-dimensional NMR spectra of the free antigen and the antigen complexed with the antigen binding peptide, such as an antibody, are compared. The antigen typically is selectively isotopically labeled with $^{15}N$ so that only signals corresponding to the antigen and no signals from the antigen binding peptide are seen in the NMR spectrum. Antigen signals originating from amino acids involved in the interaction with the antigen binding peptide typically will shift position in the spectra of the complex compared to the spectra of the free antigen, and the amino acids involved in the binding may be identified that way.

In another embodiment, epitope mapping/characterization may be done by peptide scanning. In this approach, a series of overlapping peptides spanning the full length of the polypeptide chain of an antigen are prepared and tested individually with regard to immunogenicity. The antibody titer of the corresponding peptide antigen is determined by a standard method, e.g., enzyme-linked immunosorbent assay. The various peptides can then be ranked with regard to immunogenicity, providing an empirical basis for selection of peptide design for vaccine development.

In another embodiment, protease digestion techniques may also be useful in the context of epitope mapping and identification. Antigenic determinant-relevant regions/sequences may be determined by protease digestion, e.g. by using trypsin in a ratio of about 1:50 to antigenic protein overnight (O/N) digestion at 37° C. and pH 7-8, followed by mass spectrometry (MS) analysis for peptide identification. The peptides protected from trypsin cleavage by the antigenic protein may subsequently be identified by comparison of samples subjected to trypsin digestion and samples incubated with CD38BP and then subjected to digestion by e.g. trypsin (thereby revealing a foot print for the binder). Other enzymes like chymotrypsin, pepsin, etc., may also or alternatively be used in a similar epitope characterization method. Moreover, protease digestion can provide a quick method for determining the location of a potential antigenic determinant sequence within a known antigenic protein using a known antibody. In another embodiment, protease digestion techniques may also be useful in the context of epitope mapping and identification.

Further disclosed herein is an immunogenic composition, said immunogenic composition comprising a multilayer film comprising two or more layers of polyelectrolytes, wherein adjacent layers comprise oppositely charged polyelectrolytes, wherein one layer comprises an RSV epitope. The immunogenic composition optionally further comprises one or more layers comprising a designed polypeptide.

In one embodiment, an immunogenic composition comprises a plurality of RSV epitopes, either on the same or different polyelectrolytes, for example, designed polypeptides. The plurality of antigenic determinants may be from the same or different infectious agents. In one embodiment, the immunogenic composition comprises a plurality of unique antigenic polyelectrolytes. In another embodiment, the immunogenic composition comprises a plurality of immunogenic polyelectrolytes comprising multiple RSV epitopes within each polyelectrolyte. An advantage of these immunogenic compositions is that multiple antigenic determinants or multiple conformations of a single linear antigenic determinant can be present in a single synthetic vaccine particle. Such compositions with multiple antigenic determinants can potentially yield antibodies against multiple epitopes, increasing the odds that at least some of the antibodies generated by the immune system of the organism will neutralize the pathogen or target specific antigens on cancer cells, for example.

The immunogenicity of an immunogenic composition may be enhanced in a number of ways. In one embodiment, the multilayer film optionally comprises one or more additional immunogenic bioactive molecules. Although not necessary, the one or more additional immunogenic bioactive molecules will typically comprise one or more additional antigenic determinants. Suitable additional immunogenic bioactive molecules include, for example, a drug, a protein, an oligonucleotide, a nucleic acid, a lipid, a phospholipid, a carbohydrate, a polysaccharide, a lipopolysaccharide, a low molecular weight immune stimulatory molecule, or a combination comprising one or more of the foregoing bioactive molecules. Other types of additional immune enhancers include a functional membrane fragment, a membrane structure, a virus, a pathogen, a cell, an aggregate of cells, an organelle, or a combination comprising one or more of the foregoing bioactive structures.

In one embodiment, the multilayer film optionally comprises one or more additional bioactive molecules. The one or more additional bioactive molecule can be a drug. Alternatively, the immunogenic composition is in the form of a hollow shell or a coating surrounding a core. The core comprises a variety of different encapsulants, for example, one or more additional bioactive molecules, including, for example, a drug. Thus, the immunogenic compositions designed as described herein could also be used for combined therapy, e.g., eliciting an immune response and for targeted drug delivery. Micron-sized "cores" of a suitable therapeutic material in "crystalline" form can be encapsulated by immunogenic composition comprising the antigenic polypeptides, and the resulting microcapsules could be used for drug delivery. The core may be insoluble under some conditions, for instance high pH or low temperature, and soluble under the conditions where controlled release will occur. The surface charge on the crystals can be determined by ζ-potential measurements (used to determine the charge in electrostatic units on colloidal particles in a liquid medium). The rate at which microcapsule contents are released from the interior of the microcapsule to the surrounding environment will depend on a number of factors, including the thickness of the encapsulating shell, the antigenic polypeptides used in the shell, the presence of disulfide bonds, the extent of cross-linking of peptides, temperature, ionic strength, and the method used to assemble the peptides. Generally, the thicker the capsule, the longer the release time.

In another embodiment, the additional immunogenic biomolecule is a nucleic acid sequence capable of directing host organism synthesis of a desired immunogen or interfering with the expression of genetic information from a pathogen. In the former case, such a nucleic acid sequence is, for example, inserted into a suitable expression vector by methods known to those skilled in the art. Expression vectors suitable for producing high efficiency gene transfer in vivo include retroviral, adenoviral and vaccinia viral vectors. Operational elements of such expression vectors include at least one promoter, at least one operator, at least one leader sequence, at least one terminator codon, and any other DNA sequences necessary or preferred for appropriate transcription and subsequent translation of the vector nucleic acid. In particular, it is contemplated that such vectors will contain at least one origin of replication recognized by the host organism along with at least one selectable marker and at least one promoter sequence capable of initiating transcription of the nucleic acid sequence. In the latter case, multiple copies of such a nucleic acid sequence will be prepared for delivery, for example, by encapsulation of the nucleic acids within a polypeptide multilayer film in the form of a capsule for intravenous delivery.

In construction of a recombinant expression vector, it should additionally be noted that multiple copies of the nucleic acid sequence of interest and its attendant operational elements may be inserted into each vector. In such an embodiment, the host organism would produce greater amounts per vector of the desired protein. The number of multiple copies of the nucleic acid sequence which may be inserted into the vector is limited only by the ability of the resultant vector due to its size, to be transferred into and replicated and transcribed in an appropriate host microorganism.

In a further embodiment, the immunogenic composition comprises a mixture of antigenic polyelectrolytes/immunogenic bioactive molecules. These may be derived from the same antigen, they may be different antigens from the same infectious agent or disease, or they may be from different infectious agents or diseases. The complex or mixture will therefore raise an immune response against a number of antigens and possibly a number of infectious agents or diseases as specified by the antigenic peptide/protein components of the delivery system.

In one embodiment, the multilayer film/immunogenic composition evokes a response from the immune system to a pathogen. In one embodiment, a vaccine composition comprises an immunogenic composition in combination with a pharmaceutically acceptable carrier. Thus a method of vaccination against a pathogenic disease comprises the administering to a subject in need of vaccination an effective amount of the immunogenic composition.

Pharmaceutically acceptable carriers include, but are not limited to, large, slowly metabolized macromolecules such as proteins, polysaccharides, polylactic acids, polyglycolic acids, polymeric amino acids, amino acid copolymers, inactive virus particles, and the like. Pharmaceutically acceptable salts can also be used in the composition, for example, mineral salts such as hydrochlorides, hydrobromides, phosphates, or sulfates, as well as the salts of organic acids such as acetates, proprionates, malonates, or benzoates. The composition can also contain liquids, such as water, saline, glycerol, and ethanol, as well as substances such as wetting agents, emulsifying agents, or pH buffering agents. Liposomes can also be used as carriers.

A method of eliciting an immune response against a disease or pathogen in a vertebrate (e.g., vaccination) comprises administering an immunogenic composition comprising a multilayer film comprising an RSV epitope. In one embodiment, the polyelectrolyte containing the RSV epitope is in the most exterior or solvent-exposed layer of the multilayer film. The immunogenic composition can be administered orally, intranasally, intravenously, intramuscularly, subcutaneously, intraperitoneally, sublingually, intradermally, pulmonary, or transdermally, either with or without a booster dose. Generally, the compositions are administered in a manner compatible with the dosage formulation, and in such amount as will be prophylactically and/or therapeutically effective. Precise amounts of immunogenic composition to be administered depend on the judgment of the practitioner and may be peculiar to each subject. It will be apparent to those of skill in the art that the therapeutically effective amount of an immunogenic composition will depend, inter alia, upon the administration schedule, the unit dose of antigen administered, whether the compositions are administered in combination with other therapeutic agents, and the immune status and health of the recipient. A therapeutically effective dosage can be determined by the ordinary skilled medical worker based on patient characteristics (age, weight, sex, condition, complications, other diseases, etc.), as is well known in the art. Furthermore, as further routine studies are conducted, more specific information will emerge regarding appropriate dosage levels for treatment of various conditions in various patients, and the ordinary skilled worker, considering the therapeutic context, age and general health of the recipient, is able to ascertain proper dosing.

The immunogenic composition optionally comprises an adjuvant. Adjuvants in general comprise substances that boost the immune response of the host in a non-specific manner. Selection of an adjuvant depends on the subject to be vaccinated. Preferably, a pharmaceutically acceptable adjuvant is used. For example, a vaccine for a human should avoid oil or hydrocarbon emulsion adjuvants, including complete and incomplete Freund's adjuvant. One example of an adjuvant suitable for use with humans is alum (alumina gel). A vaccine for an animal, however, may contain adjuvants not appropriate for use with humans.

It is contemplated that an immune response may be elicited via presentation of any protein or peptide capable of eliciting such a response. In one embodiment, the antigen is a key epitope, which gives rise to a strong immune response to a particular agent of infectious disease, i.e., an immunodominant epitope. If desired, more than one antigen or epitope may be included in the immunogenic composition in order to increase the likelihood of an immune response.

In one embodiment, multiple RSV peptide or protein epitopes are incorporated into an ELBL film. The distinct epitopes can by synthesized or expressed within a single designed peptide molecule. Placing multiple epitopes within a single designed peptide is expected to have certain advantages. For example it should simplify the ELBL fabrication process and increase reproducibility. Additionally, placing multiple epitopes within a single designed peptide will lock the molar ratios of the distinct epitopes in a desired ratio, for example 1:1.

Alternatively the epitopes can be incorporated into separate designed peptides. The designed peptides are incorporated into an ELBL film during one or more layering steps. Fabrication of films using multiple distinct designed peptides can also present certain advantages. It should simplify designed peptide synthesis reducing costs. It will also enable the relative doses of each designed peptide within the film to be varied and optimized. If, for example, preclinical or clinical biological data indicated that an optimal vaccine should contain five copies of one epitope to every copy of a second epitope (5:1 ratio) the separate epitope designed peptide approach would facilitate the manufacture of such a vaccine.

Designed peptides adsorb to the surface of an ELBL films by virtue of the electrostatic attraction between the charged surface adsorption regions(s) of the designed peptide and the oppositely charged surface of the film. The efficiency of adsorption will depend largely upon the composition of the surface adsorption region(s). Thus designed peptides with different epitopes but similar surface adsorption regions(s) will adsorb with similar efficiency. To fabricate a film with two distinct designed peptides each at a 1:1 molar ratio one could mix the peptides at that molar ratio and deposit them simultaneously at a particular layer. Alternatively, one could deposit each peptide individually at separate layers. The molar ratio of peptides adsorbed will largely mirror that relative concentrations at which they were layered or the number of layering steps during which they were incorporated.

The quantity of designed peptides incorporated into an ELBL film can be measured in a variety of ways. Quantitative amino acid analysis (AAA) is particularly well suited to this purpose. Films containing designed peptides are decomposed to their constituent amino acids by treatment with concentrated hydrochloric acid (6 M) and heating, typically at 115° C. for 15 hours. The amounts of each amino acid are then measured using chromatographic techniques well known to those skilled in the art Amino acids that occur in only one of the designed peptides in a film can be used as tracers for that peptide. When designed peptides lack unique amino acids, non-natural amino acids (e.g. aminobutyric acid or homovaline) can be incorporated into designed peptides during synthesis. These tracer amino acids are readily identified during the AAA experiment and can be used to quantitate the amount of peptide in the film.

As used herein, a specific T-cell response is a response that is specific to an epitope of interest, specifically an RSV epitope such as an RSV-M2 epitope as disclosed herein. A specific T-cell response may be either a cytotoxic T-cell response or a helper T-cell response, but which preferably is a cytotoxic T-cell response.

As used herein, a specific antibody response is a response that is specific to an epitope of interest, specifically an RSV epitope such as an RSV-G epitope as disclosed herein.

As used herein, "layer" means a thickness increment, e.g., on a template for film formation, following an adsorption step. "Multilayer" means multiple (i.e., two or more) thickness increments. A "polyelectrolyte multilayer film" is a film comprising one or more thickness increments of polyelectrolytes. After deposition, the layers of a multilayer film may not remain as discrete layers. In fact, it is possible that there is significant intermingling of species, particularly at the interfaces of the thickness increments. Intermingling, or absence thereof, can be monitored by analytical techniques such as potential measurements, X-ray photoelectron spectroscopy, and time-of-flight secondary ion mass spectrometry.

"Amino acid" means a building block of a polypeptide. As used herein, "amino acid" includes the 20 common naturally occurring L-amino acids, all other natural amino acids, all non-natural amino acids, and all amino acid mimics, e.g., peptoids.

"Naturally occurring amino acids" means glycine plus the 20 common naturally occurring L-amino acids, that is, alanine, valine, leucine, isoleucine, serine, threonine, cysteine, methionine, aspartic acid, asparagine, glutamic acid, glutamine, arginine, lysine, histidine, phenylalanine, ornithine, tyrosine, tryptophan, and proline.

"Non-natural amino acid" means an amino acid other than any of the 20 common naturally occurring L-amino acids. A non-natural amino acid can have either L- or D-stereochemistry.

"Peptoid," or N-substituted glycine, means an analog of the corresponding amino acid monomer, with the same side chain as the corresponding amino acid but with the side chain appended to the nitrogen atom of the amino group rather than to the α-carbons of the residue. Consequently, the chemical linkages between monomers in a polypeptoid are not peptide bonds, which can be useful for limiting proteolytic digestion.

"Amino acid sequence" and "sequence" mean a contiguous length of polypeptide chain that is at least two amino acid residues long.

"Residue" means an amino acid in a polymer or oligomer; it is the residue of the amino acid monomer from which the polymer was formed. Polypeptide synthesis involves dehydration, that is, a single water molecule is "lost" on addition of the amino acid to a polypeptide chain.

As used herein "peptide" and "polypeptide" all refer to a series of amino acids connected one to the other by peptide bonds between the alpha-amino and alpha-carboxy groups of adjacent amino acids, and may contain or be free of modifications such as glycosylation, side chain oxidation, or phosphorylation, provided such modifications, or lack thereof, do not destroy immunogenicity. As used herein, the term "peptide" is meant to refer to both a peptide and a polypeptide or protein.

"Designed polypeptide" means a polypeptide that has sufficient charge for stable binding to an oppositely charged surface, that is, a polypeptide that can be deposited into a layer of a multilayer film wherein the driving force for film formation is electrostatics. In specific embodiments, a designed polypeptide is at least 15 amino acids in length and the magnitude of the net charge per residue of the polypeptide is greater than or equal to 0.1, 0.2, 0.3, 0.4 or 0.5 at pH 7.0. In one embodiment, the ratio of the number of charged residues of the same polarity minus the number of residues of the opposite polarity to the total number of residues in the polypeptide is greater than or equal to 0.5 at pH 7.0. In other words, the magnitude of the net charge per residue of the polypeptide is greater than or equal to 0.5. While there is no absolute upper limit on the length of the polypeptide, in general, designed polypeptides suitable for ELBL deposition have a practical upper length limit of 1,000 residues. Designed polypeptides can include sequences found in nature such as RSV epitopes as well as regions that provide functionality to the peptides such as charged regions also referred to herein as surface adsorption regions, which allow the designed polypeptides to be deposited into a polypeptide multilayer film.

"Primary structure" means the contiguous linear sequence of amino acids in a polypeptide chain, and "secondary structure" means the more or less regular types of structure in a polypeptide chain stabilized by non-covalent interactions, usually hydrogen bonds. Examples of secondary structure include α-helix, β-sheet, and β-turn.

"Polypeptide multilayer film" means a film comprising one or more designed polypeptides as defined above. For example, a polypeptide multilayer film comprises a first layer comprising a designed polypeptide and a second layer comprising a polyelectrolyte having a net charge of opposite polarity to the designed polypeptide. For example, if the first layer has a net positive charge, the second layer has a net negative charge; and if the first layer has a net negative charge, the second layer has a net positive charge. The second layer comprises another designed polypeptide or another polyelectrolyte.

"Substrate" means a solid material with a suitable surface for adsorption of polyelectrolytes from aqueous solution. The surface of a substrate can have essentially any shape, for example, planar, spherical, rod-shaped, etc. A substrate surface can be regular or irregular. A substrate can be a crystal. A substrate can be a bioactive molecule. Substrates range in size from the nanoscale to the macro-scale. Moreover, a substrate optionally comprises several small sub-particles. A substrate can be made of organic material, inorganic material, bioactive material, or a combination thereof. Nonlimiting examples of substrates include silicon wafers; charged colloidal particles, e.g., microparticles of $CaCO_3$ or of melamine formaldehyde; biological cells such as erythrocytes, hepatocytes, bacterial cells, or yeast cells; organic polymer lattices, e.g., polystyrene or styrene copolymer lattices; liposomes; organelles; and viruses. In one embodiment, a substrate is a medical device such as an artificial pacemaker, a cochlear implant, or a stent.

When a substrate is disintegrated or otherwise removed during or after film formation, it is called "a template" (for film formation). Template particles can be dissolved in appropriate solvents or removed by thermal treatment. If, for example, partially cross-linked melamine-formaldehyde template particles are used, the template can be disintegrated by mild chemical methods, e.g., in DMSO, or by a change in pH value. After dissolution of the template particles, hollow multilayer shells remain which are composed of alternating polyelectrolyte layers.

A "capsule" is a polyelectrolyte film in the form of a hollow shell or a coating surrounding a core. The core comprises a variety of different encapsulants, for example, a protein, a drug, or a combination thereof. Capsules with diameters less than about 1 μm are referred to as nanocapsules. Capsules with diameters greater than about 1 μm are referred to as microcapsules.

"Cross linking" means the formation of a covalent bond, or several bonds, or many bonds between two or more molecules.

"Bioactive molecule" means a molecule, macromolecule, or macromolecular assembly having a biological effect. The specific biological effect can be measured in a suitable assay and normalizing per unit weight or per molecule of the bioactive molecule. A bioactive molecule can be encapsulated, retained behind, or encapsulated within a polyelectrolyte film. Nonlimiting examples of a bioactive molecule are a drug, a crystal of a drug, a protein, a functional fragment of a protein, a complex of proteins, a lipoprotein, an oligopeptide, an oligonucleotide, a nucleic acid, a ribosome, an active therapeutic agent, a phospholipid, a polysaccharide, a lipopolysaccharide. As used herein, "bioactive molecule" further encompasses biologically active structures, such as, for example, a functional membrane fragment, a membrane structure, a virus, a pathogen, a cell, an aggregate of cells, and an organelle. Examples of a protein that can be encapsulated or retained behind a polypeptide film are hemoglobin; enzymes, such as for example glucose oxidase, urease, lysozyme and the like; extracellular matrix proteins, for example, fibronectin, laminin, vitronectin and collagen; and an antibody. Examples of a cell that can be encapsulated or retained behind a polyelectrolyte film are a transplanted islet cell, a eukaryotic cell, a bacterial cell, a plant cell, and a yeast cell.

"Biocompatible" means causing no substantial adverse health effect upon oral ingestion, topical application, transdermal application, subcutaneous injection, intramuscular injection, inhalation, implantation, or intravenous injection. For example, biocompatible films include those that do not cause a substantial immune response when in contact with the immune system of, for example, a human being.

"Immune response" means the response of the cellular or humoral immune system to the presence of a substance anywhere in the body. An immune response can be characterized in a number of ways, for example, by an increase in the bloodstream of the number of antibodies that recognize a certain antigen. Antibodies are proteins secreted by B cells, and an immunogen is an entity that elicits an immune response. The human body fights infection and inhibits reinfection by increasing the number of antibodies in the bloodstream and elsewhere.

"Antigen" means a foreign substance that elicits an immune response (e.g., the production of specific antibody molecules) when introduced into the tissues of a susceptible vertebrate organism. An antigen contains one or more epitopes. The antigen may be a pure substance, a mixture of substances (including cells or cell fragments). The term antigen includes a suitable antigenic determinant, auto-antigen, self-antigen, cross-reacting antigen, alloantigen, tolerogen, allergen, hapten, and immunogen, or parts thereof, and combinations thereof, and these terms are used interchangeably. Antigens are generally of high molecular weight and commonly are polypeptides. Antigens that elicit strong immune responses are said to be strongly immunogenic. The site on an antigen to which a complementary antibody may specifically bind is called an epitope or antigenic determinant.

"Antigenic" refers to the ability of a composition to give rise to antibodies specific to the composition or to give rise to a cell-mediated immune response.

As used herein, the terms "epitope" and "antigenic determinant" are used interchangeably and mean the structure or sequence of an antigen, e.g., a protein or a designed peptide, which is recognized by an antibody. Ordinarily an epitope will be on the surface of a protein. A "continuous epitope" is one that involves several contiguous amino acid residues, not one that involves amino acid residues that happen to be in contact or in the limited region of space in a folded protein. A "conformational epitope" involves amino acid residues from different portions of the linear sequence of a protein that come into contact in the three-dimensional structure of the protein. For efficient interaction to occur between the antigen and the antibody, the epitope must be readily available for binding. Thus, the epitope or antigenic determinants are present in the antigen's native, cellular environment, or only exposed when denatured. In their natural form they may be cytoplasmic (soluble), membrane associated, or secreted. The number, location and size of the epitopes will depend on how much of the antigen is presented during the antibody making process.

As used herein, a "vaccine composition" is a composition which elicits an immune response in a mammal to which it is administered and which protects the immunized organism against subsequent challenge by the immunizing agent or an immunologically cross-reactive agent. Protection can be complete or partial with regard to reduction in symptoms or infection as compared with a non-vaccinated organism. An immunologically cross-reactive agent can be, for example, the whole protein (e.g., glucosyltransferase) from which a subunit peptide has been derived for use as the immunogen. Alternatively, an immunologically cross-reactive agent can be a different protein, which is recognized in whole or in part by antibodies elicited by the immunizing agent.

As used herein, an "immunogenic composition" is intended to encompass a composition that elicits an immune response in an organism to which it is administered and which may or may not protect the immunized mammal against subsequent challenge with the immunizing agent. In one embodiment, an immunogenic composition is a vaccine composition.

The invention is further illustrated by the following non-limiting examples.

EXAMPLES

Example 1

Synthesis of Designed Polypeptides (DP)

Designed polypeptides were derived from epitopes residing in sequences of the RSV-G, RSV-F or RSV-M2 proteins. The amino acid sequences of the full length proteins are as follows (selected peptide epitopes incorporated into designed polypeptides are underlined.)

RSV-G-

SEQ ID NO: 1

1 MSKNKDQRTA KTLERTWDTL NHLLFISSCL YKLNLKSVAQ ITLSILAMII STSLIIAAII 60

61 FIASANHKVT PTTAIIQDAT SQIKNTTPTY LTQNPQLGIS PSNPSEITSQ ITTILASTTP 120

121 GVKSTLQSTT VKTKNTTTTQ TQPSKPTTKQ RQNKPPSKPN NDF*HFEVFNF VPCSICSNNP* 180

181 *TCWAIC**KRIP NKKPGKKT*TTTT KPTKKPTLKT TKKDPKPQTT KSKEVPTTKP TEEPTINTTK 240

241 TNIITTLLTS NTTGNPELTS QMETFHSTSS EGNPSPSQVS TTSEYPSQPS SPPNTPRQ 298

RSV-F-

SEQ ID NO: 2

1 MELLILKANA ITTILTAVTF CFASGQNITE EFYQSTCSAV SKGYLSALRT *GWYTSVITIE* 60

61 *LSNIK*ENKCN GTDAKVKLIK QELDKYKNAV TELQLLMQST PPTNNRARRE LPRFMNYTLN 120

121 NAKKTNVTLS KKRKRRFLGF LLGVGSAIAS GVAVSKVLHL EGEVNKIKSA LLSTNKAVVS 180

181 LSNGVSVLTS KVLDLKNYID KQLLPIVNKQ SCSISNIETV IEFQQKNNRL LEITREFSVN 240

241 AGVTTPVSTY MLTNSELLSL INDMPITNDQ KKLMSNNVQI VRQQSYSIMS IIKEEVLAYV 300

301 VQLPLYGVID TPCWKLHTSP LCTTNTKEGS NICLTRT*DRG WYCDNAGSVS FFPQ*AETCKV 360

361 QSNRVFCDTM NSLTLPSEIN LCNVDIFNPK YDCKIMTSKT DVSSSVITSL GAIVSCYGKT 420

421 KCTASNKNRG IIKTFSNGCD YVSNKGMDTV SVGNTLYYVN KQEGKSLYVK GEPIINFYDP 480

481 LVFPSDEFDA SISQVNEKIN QSLAFIRKSD ELLHNVNAGK STTNIMITTI IIVIIVILLS 540

541 LIAVGLLLYC KARSTPVTLS KDQLSGINNI AFSN 574

RSV-M-

SEQ ID NO: 3

1 MSRRNPCKFE IRGHCLNGKR CHFSHNYFEW PPHALLVRQN FMLNRILKSM DKSIDTLSEI 60

61 SGAAELDRTE EYALGVVGVL *ESYIGSINNI TKQSA*CVAMS KLLTELNSDD IKKLRDNEEL 120

121 NSPKIRVYNT VISYIESNRK NNKQTIHLLK RLPADVLKKT IKNTLDIHKS ITINNPKEST 180

181 DTNDHAKN NDTT 194

Designed peptides were synthesized by stepwise solid phase peptide synthesis using a Liberty™ (CEM, Matthews, N.C.) automated synthesizer with microwave temperature control. Peptides were synthesized on either Rink Amide or Wang acid polystyrene resin support using standard Fmoc amino acids, HBTU/DIEA activation, and routine double coupling. Following synthesis resins were dried and peptides cleaved by treatment with TFA/triisopropylsilane/phenol/3,6-dioxo-1,8-octanedithiol/water (86:4:4:3:3) for two hours. Crude peptides were precipitated with ether, centrifuged, and dried under vacuum. Peptides were purified by $C_{18}$ reverse phase HPLC using a water (0.1% trifluoracetic acid)/acetonitrile gradient. The identity of each purified peptide was confirmed by electrospray mass spectrometry (ESMS). Final yields were calculated by UV absorption at280 nm and/or amino acid analysis. Peptides were aliquoted, lyophilized, and stored as trifluoroacetate salts at −20° C. until use.

Table 1 shows the selected epitopes from RSV-G, RSV-F, and RSV-M2 proteins. Each epitope was incorporated into a designed peptide (DP) by the addition of a C-terminal poly-ionic tail such as $Lys_{20}$ ($K_{20}$) or Lys-Val-Lys-Ala repeat $(KVKA)_4$ A C-terminal tyrosine was usually incorporated in order to facilitate quantitation by UV. The native sequence of RSV-M2 contains a cysteine at position 96. In the synthetic epitope peptides this residue has been replaced by a serine (C96S) in order to avoid undesired disulfide bonds at that position.

TABLE 1

Sequences and characteristics of selected RSV epitopes.

| Designation | Epitope Sequence | SEQ ID NO: | Rationale or description |
|---|---|---|---|
| $G_{164-198}$ | HFEVFNFVPCSICSNNPT **CWAIC**KRIPNK | 4 | conserved sequence containing chemokine motif associated with inflammation |
| $F_{51-65}$ | GWYTSVITIELSNIK | 5 | conserved CD4+ (Th1) epitopes that elicit IFNγ responses |
| $F_{338-354}$ | DRGWYSDNAGSVSFFRG | 6 | conserved CD4+ (Th1) epitopes that elicit IFNγ responses |
| ACT-2019 | ESYIGSINNITKQSA | 7 | $M2_{81-95}$; CD8+ T-cell target shown to modulate Th2 responses to RSV-G |
| ACT-2044 | HFEVFNFVPCSICSNNPT CWAICKRIPNKKKKKKKK KKKKKKKKKKKKKY | 8 | RSV-$G_{164-191}K_{21}$Y amide |
| ACT-2054 | HFEVFNFVPXSIXSNNPT XWAIXKRIPNKKKKKKKK KKKKKKKKKKKKKY | 9 | RSV-$G_{164-191}K_{21}$Y amide with capped cysteine residues C* = carboxamido-methylcysteine |
| $G_{175-184}$ | cyclo-ICSNNPTCWA | 10 | RSV-$G_{175-184}$ |
| ACT-2042 | NFVPCSICSNNPTCWAIC KRIPNKKKKKKKKKKKKK KKKKKKKKY | 11 | RSV-$G_{169-191}K_{21}$Y |
| ACT 2031 | ESYIGSINNITKQSASVA KVKAKVKAKVKAKVKA | 12 | RSV-$M2_{81-98}(KVKA)_4$ amide |
| ACT-2086 | ESYIGSINNITKQSASGS HFEVFNFVPCSICSNNPT CWAICKRIPNKKKKKKKK KKKKKKKKKKKKY | 13 | RSV-$M2_{81-98}G_{164-191}$ $K_{20}$Y amide |
| ACT-2087 | NFVPCSICSNNPTCWAIC KRIPNKKPGKKTKKKKKK KKKKKKKKKKKKKKY | 14 | RSV-$G_{169-198}K_{20}$Y amide |
| ACT-2088 | HFEVFNFVPCSICSNNPT CWAICKRIPNKKPGKKTK KKKKKKKKKKKKKKKKKK KY | 15 | RSV-$G_{164-198}K_{20}$Y amide |
| ACT 2033 | ESYIGSINNITKQSASVA KKKKKKKKKKKKKKKKKK KKY | 16 | RSV M2 $_{81-98}$ $K_{20}$Y amide |

Example 2

Folding and Structure Confirmation of Designed Polypeptides that Contain a Conformational Epitope from RSV-G Protein The RSV attachment protein (RSV-G protein) contains four conserved cysteine residues that form two internal disulfide bonds located within amino acids 169-191. Antibodies that recognize this region can neutralize RSV, so conformationally-restricted synthetic peptides derived from this segment may be effective vaccine components. Previous investigators have used a combination of proteolytic digestion, HPLC, and mass spectrometry to show that Cys173 is bonded to Cys186 and that Cys176 is bonded to Cys182. Peptides containing RSV-G protein residues 169-191 were synthesized by solid phase peptide synthesis. At neutral pH these peptides oxidize readily, and the resulting products appear to contain two internal disulfides as measured by the loss of four protons in the ESMS spectrum as well as by negative signal in an Ellman's (DTNB) assay. The ease with which the oxidation reactions occur and the cleanliness of the conversions are strongly suggestive that native disulfides are forming. In a typical experiment reduced RSV-G peptides (e.g. SEQ ID NO: 8, 11, 13, 14, 15) are dissolved at a concentration of 1-5 mg/mL in Tris pH 7.4 buffer containing 2.5 mM glutathione and 2.5 mM glutathiol. The folding reaction is monitored by $C_{18}$ reverse phase HPLC as the oxidized product shows a shift to slightly shorter retention time relative to the reduced peptide. By this criteria the folding reaction is judged complete after 2 hours at room temperature or after 18 hours at 4° C.

Figure 2:
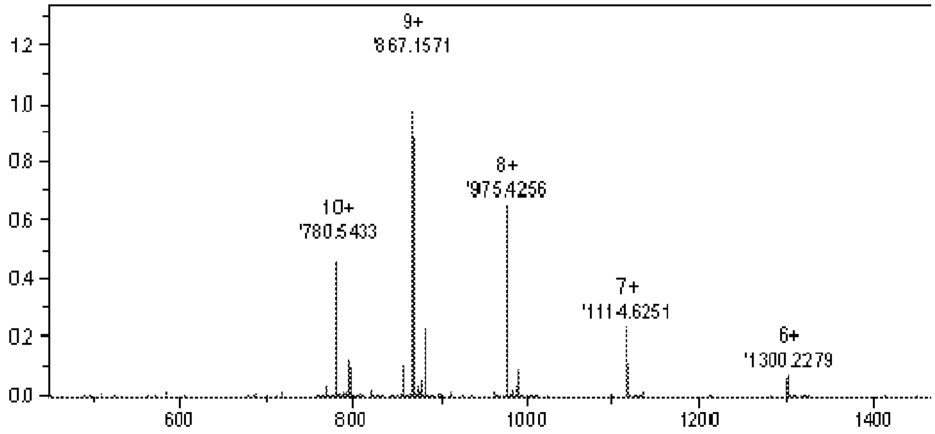
FIG. 2: FT-ICR mass spectrum for ACT-2086 (SEQ ID NO: 13). The $MH_9^{+9}$ monoisotopic peak has an m/z of 867.1571 corresponding to a monoisotopic mass of 7795.344 amu, which is very close to the calculated monoisotopic mass of 7795.33 amu. This result is fully consistent with the presence of two disulfide bonds in ACT-2086.

A sample of folded ACT-2044 (RSV-$G_{164-191}$($K_{21}$Y amide) (SEQ ID NO: 8) was analyzed using electrospray Fourier transform ion cyclotron resonance mass spectrometry (FT-ICR MS). The $MH_6^{+6}$ charge state gave a strong signal and the expanded spectrum of the $MH_6^{+6}$ peaks is shown in FIG. 1. The monoisotopic peak at mass-to-charge (m/z) 1015.6008 corresponds to a monoisotopic mass of 6087.56 amu, which is very close to the calculated monoisotopic mass of 6088.51 amu, and this result is fully consistent with the presence of two disulfide bonds in ACT-2044. Likewise a sample of folded ACT-2086 (RSV-$M2_{81-98}$ $G_{164-191}K_{20}$Y amide (SEQ ID NO: 13) was analyzed by FT-ICR MS and the spectrum is shown in FIG. 2. Strong peaks were observed for the $MH_6^{+6}$-$MH_{10}^{+10}$ charge states. The $MH_9^{+9}$ monoisotopic peak had a m/z of 867.1571 corresponding to a monoisotopic mass of 7795.344 amu, which is very close to the calculated monoisotopic mass of 7795.33 amu. Again this result is fully consistent with the presence of two disulfide bonds.

A sample of ACT-2044 (RSV$_{-G164-191K21}$Y) (SEQ ID NO: 8) was subjected to thermolysin digestion. HPLC analysis of the digest demonstrated complete consumption of the starting peptide. The FT-ICR spectrum of this product contained a complex mixture of products, but a dominant ion was found at m/z 1106.4. This species corresponds to the $MH^{+1}$ charge state for intramolecular disulfide bonded RSV-$G_{175-184}$ (cyclo-ICSNNPTCWA (SEQ ID NO: 10), expected $MH^+$ mass=1106.440, found=1106.438). This peptide is diagnostic for the native disulfide bond between Cys176 and Cys182. In summary, the FT-ICR MS data strongly support the claim that ACT-2044 (and closely related peptides ACT-2042, (SEQ ID NO: 11), ACT-2086, (SEQ ID NO: 13), ACT-2087, (SEQ ID NO: 14), ACT-2088, (SEQ ID NO: 15)) contain two internal disulfide bonds in the correct (native) pattern.

Example 3

General Procedure for Fabrication of ELBL Nanoparticles $CaCO_3$ nanoparticles (NPCC-111) were obtained from NanoMaterials Technology (Singapore). Scanning electron microscopy (SEM) experiments showed particles have a cubic morphology and are approximately 50 nm in diameter. Polypeptides poly-1-lysine 15 kDa (PLL, catalog # P6516), poly-1-glutamic acid 14.5 kDa (PGA, catalog #P4636), and 1 M HEPES buffer solution (catalog #H-3662) were obtained from Sigma-Aldrich (USA). Oppositely charged polypeptides were allowed to self-assemble into a multilayer film on $CaCO_3$ nanoparticle cores in successive adsorption steps. Briefly, PLL, PGA or designed polypeptide (DP, where indicated) were dissolved to 1 mg/ml (weight/volume) in 10 mM HEPES, pH 7.4, and filtered through a 0.22 μm filter. $CaCO_3$ nanoparticle cores were washed three times with endotoxin-free water and centrifuged at 16,000 g for 1 minute in a microcentrifuge. Nanoparticle cores were resuspended to 6% (weight/volume) in 1 mg/ml PGA as the first layer. At neutral pH, PGA exhibits a net negative charge while the $CaCO_3$ particles are net positive, thus enabling electrostatic interaction and successful deposition of the first layer. The mixture was sonicated for 10 minutes at room temperature, then washed twice with 10 mM HEPES buffer and centrifugation at 48,700×g for 1 minute (TL-100 Ultracentrifuge, Beckman). For second layer deposition, the nanoparticles were resuspended to 6% (w/v) in 1 mg/ml PLL (positive charge) and sonicated for 10 minutes at room temperature as for the first layer. Each subsequent layer was deposited by the same method, using PGA, PLL, or DP as indicated in Table 2 or Table 3. Typically designed peptides were coated at a concentration of 0.5-1.0 mg/mL. Following the final layer deposition, the nanoparticles were washed twice with 10 mM HEPES, pH 7.4, and aliquots were spun down, aspirated, and stored as damp pellets at 4° C. until use. Several designs were produced using essentially the same procedure and altering the sequence and location of the designed peptide; all nanoparticles contain a total of eight layers in the polypeptide biofilm. Nanoparticle designs are summarized in Table 2. The concentration of polypeptide or DP on the nanoparticles was determined by amino acid analysis. Nanoparticle size was determined by dynamic light scattering (Malvern Nano S-90) of 0.06% (w/v) suspensions in HEPES, pH 7.4, sonicated for 20 minutes in an ultrasonic water bath (Branson 1510, USA) prior to measurement. Levels of endotoxin in the nanoparticles were determined by Limulus Amebocyte Lysate assay, an endpoint chromogenic assay (#50-647U, Lonza, Walkersville, Md.). The prepared nanoparticles were stored as a damp pellet at 4° C. until ready for use.

TABLE 2

Monovalent nanoparticle designs.

| ACT # | Layers | DP ACT # | DP sequence |
|---|---|---|---|
| 1023 | PGA/PLL/PGA/RSV-M2/PGA/PLL/PGA/PLL | 2031 | RSV-$M2_{81-98}$(KVKA)$_4$ (SEQ ID NO: 12) |
| 1041 | PGA/PLL/PGA/PLL/PGA/PLL/PGA/RSV-G | 2042 | RSV-$G_{169-191}K_{21}$Y (SEQ ID NO: 11) |

TABLE 2-continued

| Monovalent nanoparticle designs. | | | |
|---|---|---|---|
| ACT # | Layers | DP ACT # | DP sequence |
| 1042 | PGA/PLL/PGA/PLL/PGA/PLL/PGA/RSV-G | 2044 | RSV-$G_{164-191}K_{21}Y$ (SEQ ID NO: 8) |

ACT # refers to designation of distinct nanoparticle designs. DP # refers to distinct designed peptides. DP sequence lists the specific RSV epitopes and polyionic tail included in each DP.

Example 4

Fabrication and Characterization of ELBL Nanoparticle ACT-1077

Figure 3:
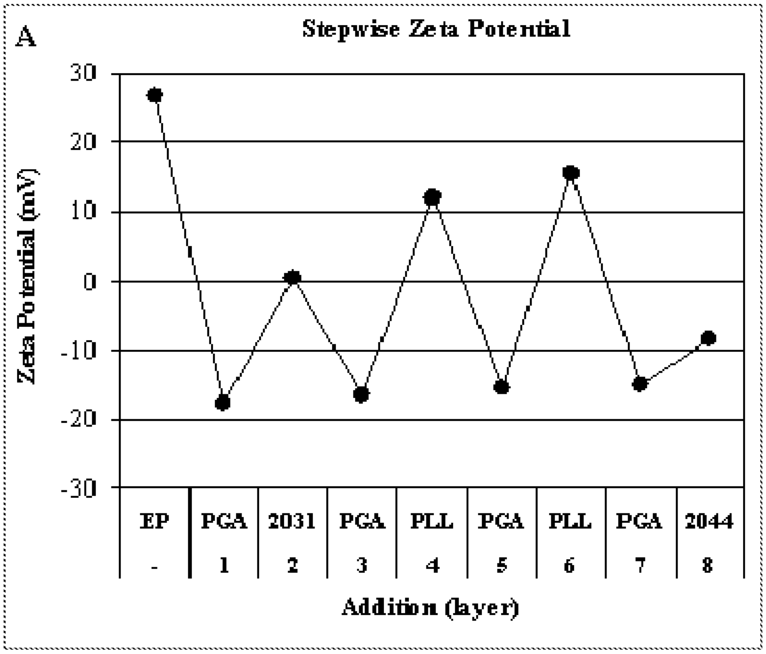
FIG. 3: Surface (zeta) potential of nanoparticles measured after each ELBL layering step. Uncoated particles (EP) have a positive zeta value. Coating with a single layer of PGA imparts a negative zeta value. Subsequent layering steps with designed peptide ACT-2031, polypeptides PGA and PLL, or designed peptide ACT-2044 causes alternating positive or negative shifts in zeta potential, indicating successful ELBL steps.

The standard procedure described in Example 3 was followed. A 1.0 mg/mL solution of designed peptide ACT-2031 (RSV-$M2_{81-98}(KVKA)_4$ (SEQ ID NO:12)) was used during the second ELBL coating step and a 1.0 mg/mL solution of designed peptide ACT-2044 (RSV-$G_{164-191}K_{21}Y$ (SEQ ID NO:8)) was used during the eighth ELBL step. After each layering step nanoparticles were washed and resuspended to 6%. A 10 μL aliquot was removed and diluted into 1.0 mL of 10 mM HEPES buffer for surface (zeta) potential analysis. FIG. 3 shows the surface zeta potentials measured for the nanoparticles at each step of the ELBL process. Before coating the $CaCO_3$ particles displayed a positive surface potential of about +28 mV. After coating with a single layer of PGA, a negative surface potential of −18 mV was measured. Coating with ACT-2031 (SEQ ID NO:12) at the second layer increased the zeta potential to about 0 mV, indicating adsorption of the peptide. Thereafter, each layering step effected a negative or positive shift in zeta potential, indicating successful ELBL adsorption. After fabrication the amount of each designed peptide adsorbed was calculated from the signal from unique amino acids in the amino acid chromatogram. Glycine is unique to ACT-2031 and can be used to determine ACT-2031 concentration while arginine, histidine, and phenylalanine are unique to ACT-2044 and can be used to determine ACT-2044 concentration. From four separate batches the average amounts of ACT-2031 and ACT-2044 adsorbed to a 1% $CaCO_3$ particle suspension were 21 μg/mL and 53 μg/mL, respectively.

Example 5

Fabrication of ELBL Nanoparticle ACT-1086

The ELBL coating procedure described in Example 3 was used to coat 50 nm $CaCO_3$ nanoparticles with seven layers of PGA and PLL. A 0.5 mg/mL solution of designed peptide ACT-2086 (SEQ ID NO: 13; RSV-$M2_{81-98}G_{164-191}K_{20}Y$ amide) in 10 mM HEPES buffer was used to coat the final layer. The amount of designed peptide adsorbed was measured by amino acid analysis. From three separate batches the average amount of ACT-2086 adsorbed to a 1% CaCO3 particle suspension was 37 μg/mL.

Example 6

Fabrication of ELBL Nanoparticle ACT-1139

The ELBL coating procedure described in Example 3 was used to coat 50 nm $CaCO_3$ nanoparticles with seven layers of PGA and PLL. A 10 mM HEPES solution of designed peptides ACT-2033 (SEQ ID NO: 16; RSV $M2_{81-98}K_{20}Y$ amide) and ACT-2044 (SEQ ID NO: 8; RSV-$G_{161-191}K_{21}Y$ amide) each at a final concentration of 0.25 mg/mL was used to coat the final layer. Nanoparticles were washed, spun, and stored as damp pellets at 4° C. The amounts of each designed peptide adsorbed were calculated from the signal from unique amino acids in the amino acid chromatogram. Glycine is unique to ACT-2033 and can be used to determine ACT-2033 concentration while arginine, histidine and phenylalanine are unique to ACT-2044 and can be used to determine ACT-2044 concentration. From this analysis it was determined that a 1% particle suspension contained 25 μg/mL ACT-2033 and 24 μg/mL ACT-2044.

Example 7

Fabrication of ELBL Microparticle ACT-1145

Mesoporous 3 μm $CaCO_3$ microparticles were obtained from PlasmaChem GmbH (Berlin, catalog # PL-CA3). Particles were suspended to 6% (weight/volume) in 10 mM HEPES. The ELBL coating procedure described for $CaCO_3$ nanoparticles in Example 3 was used with the following modifications. 3 μm $CaCO_3$ microparticles readily settle under normal gravity in aqueous suspension so instead of sonication during the layering steps the suspensions were gently mixed on a rotator for 10 minutes. Also, slower centrifugation speeds can be used to pellet microparticles following layering and washing steps. Thus microparticle suspensions were spun at 1500 g for 1 minute. For the fabrication of ACT-1145 a 1.0 mg/mL solution of PGA was used to coat the first layer and a 1.0 mg/mL layer of PLL labeled with fluorescein (PLL-FITC, Sigma catalog # P3543) was used for the second layer. PGA and PLL were used for the next five layering steps to coat the microparticles with a total of seven polypeptide layers (These particles can be used in an amide cross linking experiment as described in Example 8). A 0.5 mg/mL solution of ACT-2086 (SEQ ID NO: 13; RSV-$M2_{81-98}G_{164-191}K_{20}Y$ amide) was used to coat the final layer. Microparticles were washed, spun, and stored as damp pellets at 4° C. The amount of ACT-2086 adsorbed to the particles was calculated by amino acid analysis and found to be 43 μg/mL for a 1% particle suspension. Particles were examined by fluorescence microscopy and found to be spherical with diameters of 3.0 (+/−1.5) μm. Particles were well dispersed single particles with a few aggregates of two or three particles.

Example 8

Fabrication of ELBL Microparticle ACT-1146

The procedure in Example 7 was used to fabricate 3 μm $CaCO_3$ microparticles with seven polypeptide layers (PGA/PLL-FITC/PGA/PLL/PGA/PLL/PGA). A solution of 0.2 M sodium phosphate pH 6.5 buffer containing 38 mg/mL (0.20 M) 1-ethyl-3-(3-dimethylaminopropyl) carbodiimide (EDC, Sigma catalog # E6383) and 11 mg/mL (0.05 M) N-hydroxysulfosuccinimide sodium salt (sulfo-NHS, Sigma catalog #56485) was freshly prepared. The seven layer microparticles were suspended in the EDC/sulfo-NHS solution to a 3% suspension. The suspension was gently mixed for 30 minutes at room temperature, then the particles were spun and washed three times with 10 mM HEPES buffer. A 0.5 mg/mL solution of ACT-2086 (SEQ ID NO: 13; RSV-$M2_{81-98}G_{164-191}$ $K_{20}Y$ amide) was used to coat the final layer. Microparticles were washed, spun, and stored as damp pellets at 4° C. The amount of ACT-2086 adsorbed to the particles was calculated by amino acid analysis and found to be 49 μg/mL for a 1% particle suspension.

Example 9

Fabrication of ELBL Microcapsule ACT-1147

$CaCO_3$ microparticles ACT-1146 from Example 8 were suspended to 6% (weight/volume) in 0.5 M sodium EDTA, pH 8.0 solution. The particles were gently mixed at room temperature for 30 minutes, centrifuged for 3 minutes at 1500 g, and the EDTA solution aspirated. The resulting microcapsules were twice resuspended in 10 mM HEPES buffer and centrifuged for 3 minutes at 1500 g to remove excess salts. Microcapsules were spun, aspirated and stored as a damp pellet at 4° C. The amount of ACT-2086 adsorbed to the capsules was calculated by amino acid analysis and found to be 41 μg/mL for a 1% particle suspension. Capsules were examined by fluorescence microscopy and found to be spherical with diameters of 3.0 (+/−1.5) μm. Capsules were well dispersed single capsules with a few aggregates of two or three capsules.

Example 10

Immunogenicity of RSV-G Monovalent Nanoparticles

Figure 4:
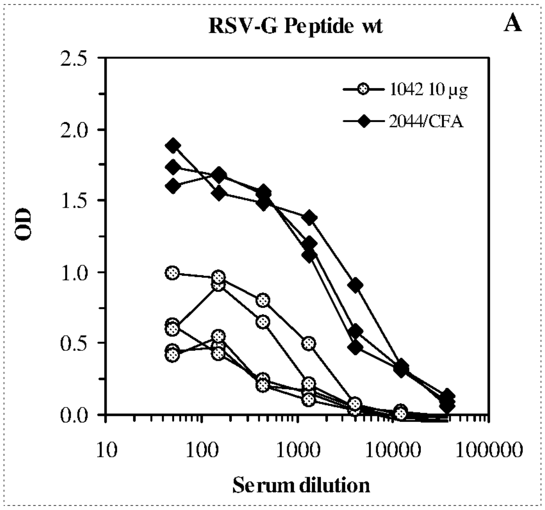
FIG. 4: Immunization of BALB/c mice three times with nanoparticle ACT-1042 (SEQ ID NO: 8; $RSV\text{-}G_{164\text{-}191}$) via footpad injection; sera were harvested and tested by ELISA. The sera recognized the conformational RSV-G CX3C epitope peptide ACT-2044 (SEQ ID NO: 8).
Figure 5:
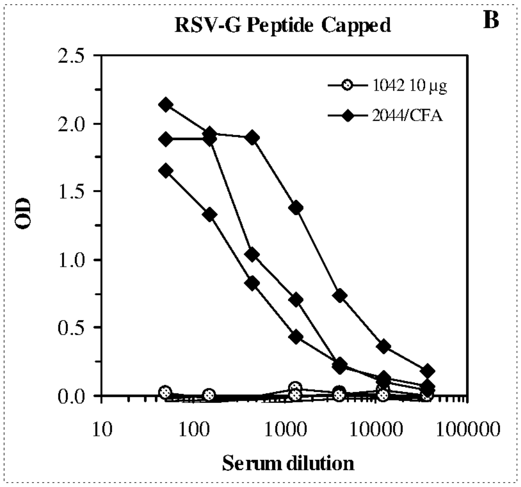
FIG. 5: Immunization of BALB/c mice three times with nanoparticle ACT-1042 (SEQ ID NO: 8; $RSV\text{-}G_{164\text{-}191}$) via footpad injection; sera were harvested and tested by ELISA. The sera did not recognize a version of the same peptide (ACT-2054; SEQ ID NO: 9) that was linearized by capping the cysteine residues.
Figure 6:
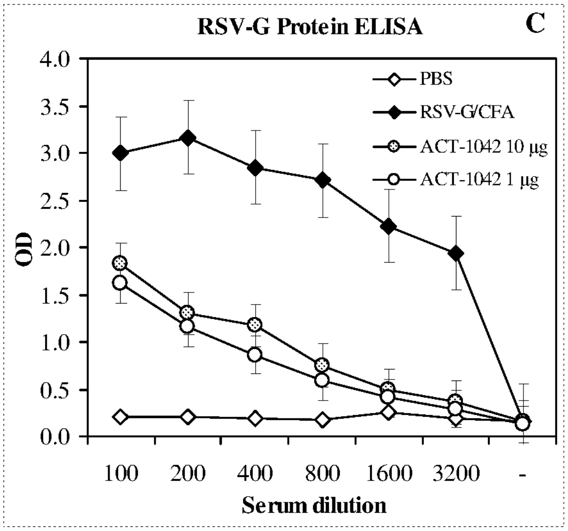
FIG. 6: Immunization of BALB/c mice three times with nanoparticle ACT-1042 (SEQ ID NO: 8; $RSV\text{-}G_{164\text{-}191}$) via footpad injection; sera were harvested and tested by ELISA. The sera also recognized native RSV-G protein.
Figure 7:
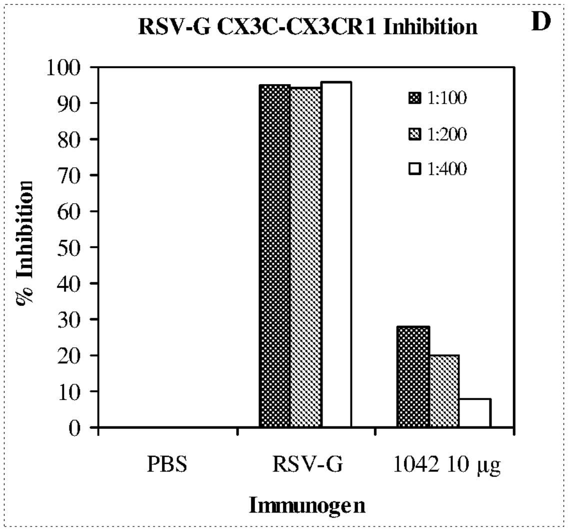
FIG. 7: Immunization of BALB/c mice three times with nanoparticle ACT-1042 (SEQ ID NO: 8; RSV-$G_{164-191}$) via footpad injection; sera were harvested and tested in a biochemical binding assay measuring inhibition of RSV-G binding to the CX3CR1 chemokine receptor. The biological activity of the antibody response elicited by ACT-1042 was confirmed by inhibition of binding of RSV-G to the chemokine receptor.
Figure 8:
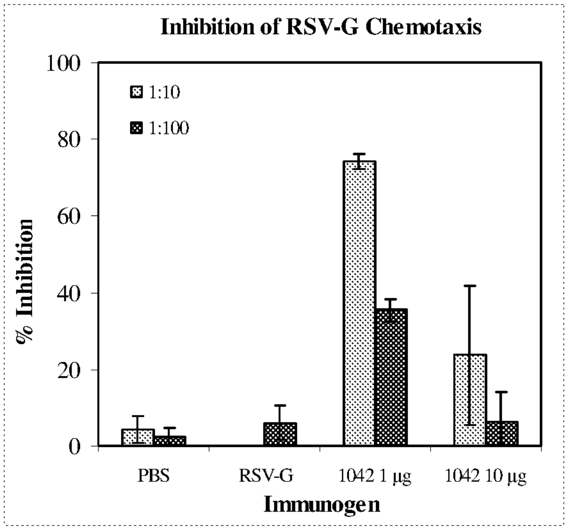
FIG. 8: Immunization of BALB/c mice three times with nanoparticle ACT-1042 (SEQ ID NO: 8; RSV-$G_{164-191}$) via footpad injection; sera were harvested and tested in a cellular migration assay. The biological activity of the antibody response elicited by ACT-1042 was confirmed by inhibition of migration of human PBMC toward purified RSV-G.

BALB/c mice were immunized three times with nanoparticle ACT-1042 (DP SEQ ID NO: 8; RSV-$G_{164-191}$) via footpad injection, and sera were harvested and tested by ELISA. The sera recognized the conformational RSV-G CX3C epitope peptide ACT-1042 (FIG. 4), but not a version of the same peptide (ACT-2054) that was linearized by capping the cysteine residues (FIG. 5). The sera also recognized native RSV-G protein (FIG. 6), suggesting that immunization with the RSV-G ELBL nanoparticle elicited conformation-dependent antibody responses. The biological activity of the antibody response elicited by ACT-1042 was confirmed in assays measuring inhibition of RSV-G CX3C chemokine binding (FIG. 7) and inhibition of migration of human PBMC toward purified RSV-G (FIG. 8). Thus, a novel nanoparticle vaccine design that incorporates a designed peptide based on the conformationally constrained RSV-G CX3C epitope can elicit biologically relevant antibody responses.

Example 11

Immunogenicity of RSV-M2 Monovalent Nanoparticles

Figure 9:
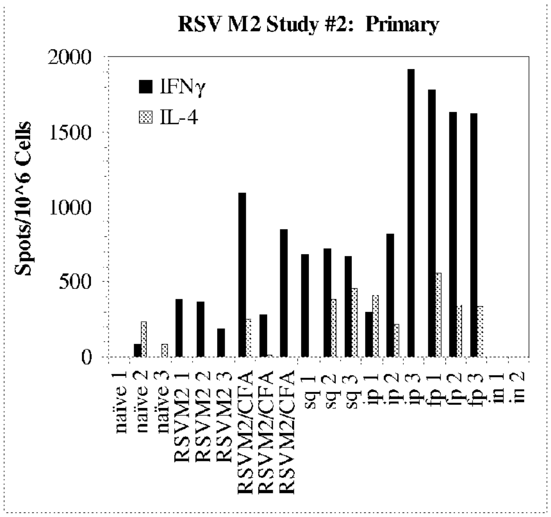
FIG. 9: RSV M2-specific T-cell responses following immunization with ACT-1023 (SEQ ID NO: 12; RSV-$M2_{81-98}$) via s.c., i.p., i.n., and food pad administration. Splenocytes were harvested from the mice on day 14 post-immunization and re-stimulated in IL-4 or IFNγ ELISPOT plates with ACT-2019 (SEQ ID NO: 7), the RSV-M2 peptide. Results reflect the number of antigen-specific T-cells/$10^6$ cells in individual naïve or immunized animals.

BALB/c mice were immunized with nanoparticle ACT-1023 (RSV-$M2_{81-98}$) (DP SEQ ID NO:12) via s.c. (subcutaneous), i.p. (intraperitoneal), i.n. (intranasal), or foot pad. Positive control mice were immunized s.c. with peptide ACT-2019 (RSV-$M2_{81-95;}$ SEQ ID NO: 7) in complete Freund's adjuvant (CFA) and boosted with ACT-2019 in incomplete Freund's adjuvant (IFA); naïve mice served as negative controls. T-cell responses in the spleens were measured in IL-4 and IFNγ ELISPOT assays 14 days post-immunization. The data in FIG. 9 show that immunization with ACT-1023 induced weak IL-4 ELISPOTs, as expected for the CD8 epitope contained in the DP. By contrast, mice immunized via the footpad yielded vigorous IFNγ responses following a single immunization. The s.c. and i.p. groups yielded less potent responses that were still comparable to the positive control CFA group. Intranasal delivery does not appear to be immunogenic in this experiment. Immunization with peptide alone yielded low levels of IFNγ responses. Thus, we have confirmed that the potency of the RSV-M2 peptide is significantly increased by embedding it in an ELBL nanoparticle.

Example 12

Figure 10:
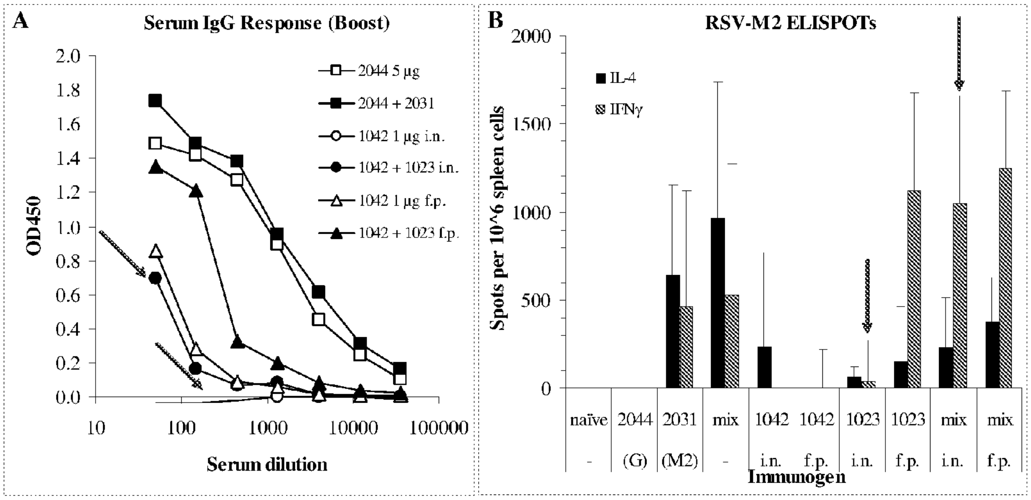
FIG. 10: Immunogenicity of multivalent RSV nanoparticle cocktail vaccine. BALB/c mice (5/group, 5-6 weeks old) were immunized on days 0 and 21. Antibody responses to RSV-G: Sera were collected on day 28 and RSV-G-specific IgG antibody titers were measured by ELISA. The data depict the mean±SD of 5 mice per group.

Improved Immunogenicity of RSV-G and RSV-M2 Nanoparticles when Combined in a Multivalent Cocktail Vaccine Immunization of mice with either monovalent nanoparticle vaccine elicited the predicted immune responses (see FIGS. 4-8 and 9). It is interesting to note that the antibody responses depicted in FIGS. 4-8 required three immunizations (prime+two boosts) while the T-cell responses depicted in FIG. 9 required only a single immunization (prime). To determine whether a multivalent nanoparticle vaccine containing both RSV-G and RSV-M2 could improve the immune potency of the RSV-G component, mice were immunized with a mixture of RSV-G (ACT-1042, 1 μg DP per dose) and RSV-M2 (ACT-1023, 5 μg DP per dose) nanoparticles delivered via either the foot pad or intranasally. Post-prime and post-boost antibody titers were measured by ELISA and post-boost T-cell responses were monitored by ELISPOT. None of the mice that received any of the constructs had a measurable primary antibody response (data not shown). FIG. 10 shows the results from the post-boost ELISA measuring RSV-G-specific IgG. In mice that received only ACT-1042, only administration via the footpad resulted in a detectable titer. Addition of the RSV-M2 nanoparticle in the footpad group yielded antibody titers equal to those induced by 5 μg of RSV-G peptide in CFA. The intranasal administration of the mixture elicited titers nearly the same as f.p. injection of the RSV-G nanoparticle alone, while i.n. administration of RSV-G nanoparticle alone failed to elicit detectable antibody titers on boost. These results demonstrate that inclusion of the RSV-M2 nanoparticle appears to increase the potency of the antibody epitope in RSV-G and that i.n. administration of nanoparticle can elicit an immune response.

T-cell responses of the same mice were measured by ELISPOT. FIG. 11 shows that mice immunized via the f.p. with the RSV-M2-containing nanoparticle or the cocktail mounted a T-cell response against the M2 epitope that was almost entirely IFNγ, as expected. When administered intranasally, the RSV-M2 nanoparticle alone (ACT-1023) failed to elicit a T-cell response. By contrast, co-administration of the RSV-M2 and RSV-G nanoparticles (mix) elicited a potent IFNγ response that was comparable to that induced by footpad immunization with RSV-M2 alone.

Figure 12:
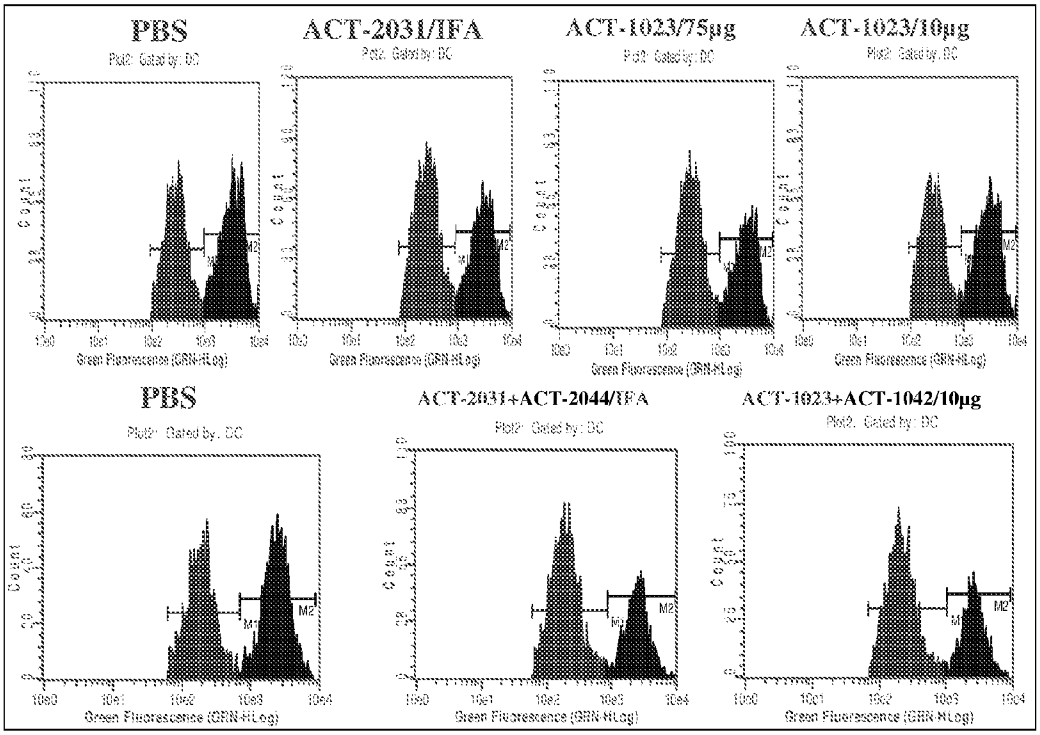
FIG. 12: Induction of in vivo CTL activity by RSV nanoparticle immunization, BALB/c mice were immunized as shown and challenged 7 days later by i.v. injection of syngeneic spleen cells pulsed with ACT-2031 (RSV-M2; SEQ ID NO: 12) and labeled with a high dose of fluorescent tracer CFSE (rightmost peak in each panel) mixed with syngeneic spleen cells labeled with a low dose of CFSE and no target peptide (leftmost peak in each panel). The next day, spleens of the immunized mice were analyzed by flow cytometry to detect survival of the differentially-labeled donor target cells. Each histogram shows the results from a single immunized mouse in that treatment group.
Figure 13:
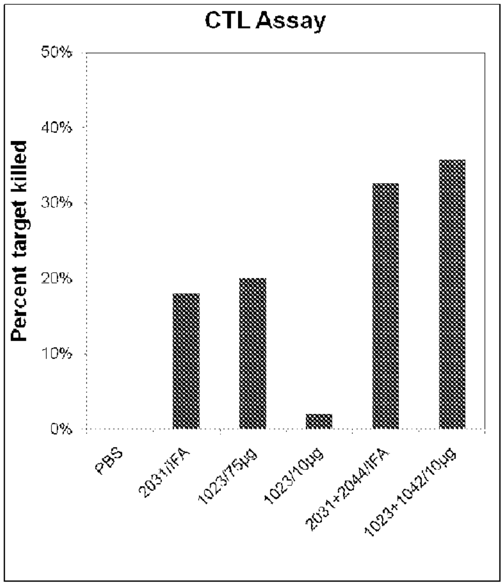
FIG. 13: Induction of in vivo CTL activity by RSV nanoparticle immunization. Results show percent specific killing of RSV-M2-labeled target cells in FIG. 12 calculated by comparing the relative number of cells in each peak within a histogram.

T-cell responses were also examined in an in vivo CTL assay which measures the activity of cytotoxic T-cells in the host animal. In the monovalent cohort, BALB/c mice were immunized via the footpad with a single injection of PBS (negative control), peptide ACT-2031 (RSV-M2) in incomplete Freund's adjuvant (IFA), or nanoparticle ACT-1023 (RSV-M2). In the multivalent cohort, mice were immunized with PBS, peptide ACT-2031 (RSV-M2) plus peptide ACT-2044 (RSV-G) in IFA, or ACT-1023 (RSV-M2) plus ACT-1042 (RSV-G). Seven days later, RSV-M2 target cells were prepared by pulsing syngeneic naïve spleen cells with peptide ACT-2031 and labeling with a high dose of fluorescent tracer CFSE, while control target cells were prepared by labeling syngeneic naïve spleen cells with a low dose of CFSE and no target peptide. The two CFSE-labeled cell populations were mixed at a 1:1 ratio, and $5\times10^6$ cells were injected i.v. into the immunized mice where they homed to the host spleen. After 24 hours, the immunized mice were sacrificed and their spleen cells were analyzed for CFSE fluorescence to monitor survival of the two cell populations. In FIG. 12, the left-most peaks in the histograms represent the surviving control target cells and the right-most peaks represent the surviving RSV-M2-labeled target cells. As expected, both cell populations survived equally in the non-immune (PBS) mice. By contrast, in mice immunized with peptide ACT-2031/IFA, approximately 18% of the RSV-M2 target cells were killed (compare size of right peak to size of left peak in ACT-2031/IFA histogram). Similar results were obtained in the mice immunized with a high dose (75 μg) of nanoparticle ACT-1023, compared to no killing of labeled target cells in mice immunized with a lower dose (10 μg) of ACT-1023. In the mice immunized with a combination of the two peptides or the two nanoparticles, a greater degree of killing of labeled target cells was observed. Specifically, mice immunized with the cocktail of nanoparticles (ACT-1023+ACT-1042 at 10 μg each) killed 35% of the RSV-M2-labeled target cells, which is higher than the response induced even by a high dose of monovalent immunization (ACT-1023/75 μg). The percent specific killing of RSV-M2-labeled target cells is summarized in FIG. 13. These results agree with the increased IFNγ ELISPOT numbers detected in mice immunized with the cocktail of RSV-G and RSV-M2 nanoparticles (see FIG. 10, 11). These data suggest that combining RSV-G and RSV-M2 nanoparticles into a cocktail vaccine provides a mutual improvement in immune potency of both components. While the improvement in the antibody response to RSV-G (FIG. 10) might be attributed to T-cell help elicited by RSV-M2, the reciprocal improvement in the T-cell response to RSV-M2 following intranasal administration of the cocktail (FIG. 11) was unexpected.

Example 13

Design of Multivalent Nanoparticles

Additional nanoparticles were designed to include multiple epitopes in the same particle, either as separate DP co-layered in the same particle or as a fusion DP containing both RSV-G and RSV-M2 epitopes. Table 3 describes the architecture of multiple epitope RSV nanoparticles, and Table 4 describes the DP sequences used in each. Nanoparticles ACT-1077 thru -1079 contain the T-cell epitope of RSV-M2 at one or multiple layers and the B-cell epitope of RSV-G at the $8^{th}$ layer. Nanoparticles ACT-1086 thru -1088 contain dual epitope peptides ACT-2086 thru -2088, respectively, deposited at the $8^{th}$ layer only. Additional designs can be envisioned using these or other RSV epitopes either co-layered or in a single fusion peptide.

TABLE 3

Architecture of multivalent RSV nanoparticles, RSV microparticles, and RSV microcapsules designs.

| ACT # | Layers | DP ACT # | DP sequence |
|---|---|---|---|
| 1077 | PGA/RSV-M2/(PGA/PLL)$_2$/PGA/RSV-G | 2031<br>2044 | RSV-M2$_{81-98}$(KVKA)$_4$ (SEQ ID NO: 12)<br>RSV-G$_{164-191}$K$_{21}$Y (SEQ ID NO: 8) |
| 1078 | (PGA/RSV-M2)$_2$/PGA/PLL/PGA/RSV-G | 2031<br>2044 | RSV-M2$_{81-98}$(KVKA)$_4$ (SEQ ID NO: 12)<br>RSV-G$_{164-191}$K$_{21}$Y (SEQ ID NO: 8) |
| 1079 | (PGA/RSV-M2)$_3$/PGA/RSV-G | 2031<br>2044 | RSV-M2$_{81-98}$(KVKA)$_4$ (SEQ ID NO: 12)<br>RSV-G$_{164-191}$K$_{21}$Y (SEQ ID NO: 8) |
| 1086 | (PGA/PLL)$_3$/PGA/RSV-G + M2 | 2086 | RSV-M2$_{81-98}$G$_{164-191}$K$_{20}$Y (SEQ ID NO: 13) |
| 1087 | (PGA/PLL)$_3$/PGA/RSV-G | 2087 | RSV-G$_{169-198}$K$_{20}$Y (SEQ ID NO: 14) |
| 1088 | (PGA/PLL)$_3$/PGA/RSV-G | 2088 | RSV-G$_{164-198}$K$_{20}$Y (SEQ ID NO: 15) |
| 1139 | PGA/PLL/PGA/PLL/PGA/PLL/PGA/RSV-M2 + RSV-G mixed | 2033<br>2044 | RSV M2 $_{81-98}$ K$_{20}$Y (SEQ ID NO: 16)<br>RSV-G$_{164-191}$K$_{21}$Y (SEQ ID NO: 8) |

TABLE 3-continued

Architecture of multivalent RSV nanoparticles, RSV microparticles, and RSV microcapsules designs.

| ACT # | Layers | DP ACT # | DP sequence |
|---|---|---|---|
| 1145 | PGA/PLL-FITC/PGA/PLL/PGA/PLL/PGA/RSV-G | 2086 | RSV-M2$_{81-98}$G$_{164-191}$ K$_{20}$Y (SEQ ID NO: 13) |
| 1146 | PGA/PLL-FITC/PGA/PLL/PGA/PLL/PGA/RSV-G | 2086 | RSV-M2$_{81-98}$G$_{164-191}$ K$_{20}$Y (SEQ ID NO: 13) |
| 1147 | PGA/PLL-FITC/PGA/PLL/PGA/PLL/PGA/RSV-G | 2086 | RSV-M2$_{81-98}$G$_{164-191}$ K$_{20}$Y (SEQ ID NO: 13) |

ACT-1077 through -1079 contain two separate DP deposited on distinct layers in the same ELBL nanoparticle. ACT-1139 contains two separate DP deposited at the 8$^{th}$ layer in the same ELBL nanoparticle. ACT-1086 through -1088 contain a single fusion peptide incorporating both antibody and T-cell target epitopes deposited on the 8$^{th}$ layer of an ELBL nanoparticles. ACT-1145 and -1146 contain a single fusion peptide incorporating both antibody and T-cell target epitopes deposited on the 8$^{th}$ layer of ELBL microparticles. ACT-1147 contains a single fusion peptide incorporating both antibody and T-cell target epitopes deposited on the 8$^{th}$ layer of ELBL microcapsules.

TABLE 4

RSV DP sequences used in multivalent ELBL nanoparticle designs in Table 3.

| | M2 protein seq. | link | G protein sequence | tail |
|---|---|---|---|---|
| ACT 2031 | **ESYIG SINNIT KQSA***S VA* SEQ ID NO: 12 | | | (KVKA)$_4$ SEQ ID NO: 16 |
| ACT 2033 | **ESYIG SINNIT KQSA***S VA* SEQ ID NO: 12 | | | K$_{20}$Y SEQ ID NO: 17 |
| ACT 2042 | | | NFVPCSICSNNPTCWAICKRIPN SEQ ID NO: 18 | K$_{21}$Y SEQ ID NO: 19 |
| ACT-2044 | | | HFEVFNFVPCSICSNNPTCWAICKRIPN SEQ ID NO: 20 | K$_{21}$Y |
| ACT-2086 | **ESYIG SINNIT KQSA** SEQ ID NO: 7 | *SGS* | HFEVFNFVPCSICSNNPTCWAICKRIPN SEQ ID NO: 21 | K$_{20}$Y |
| ACT-2087 | | | NFVPCSICSNNPTCWAICKRI**PNKKPGKKT** SEQ ID NO: 22 | K$_{20}$Y |
| ACT-2088 | | | HFEVFNFVPCSICSNNPTCWAICKRI**PNKKPGKKT** SEQ ID NO: 23 | K$_{20}$Y |

B-cell epitopes shown in underline, T-cell epitopes shown in bold, conserved cysteines shaded, non-native sequence shown in italics.

Example 14

Dose-Dependence of DP-Nanoparticle Constructs

The same dose of designed peptide (1 μg) was used in both the positive control (CFA) and the nanoparticle (1042) groups. In previous experiments, 5-10 μg was used for the CFA and 1 μg for the nanoparticle. These results show that at equivalent doses the nanoparticles are more immunogenic than the CFA control.

TABLE 5

Groups for RSV mixing study

| Group | Description |
|---|---|
| 1 | Naive |
| 2 | (ACT-2044 + ACT-2031)/CFA(IFA) s.c |
| 3 | ACT-1042 1 μg f.p. |
| 4 | ACT-1042 1 μg + ACT-1023 1 μg f.p. |
| 5 | ACT-1077 1 μg f.p. |
| 6 | ACT-1078 1 μg f.p. |
| 7 | ACT-1079 1 μg f.p. |

Figure 14:
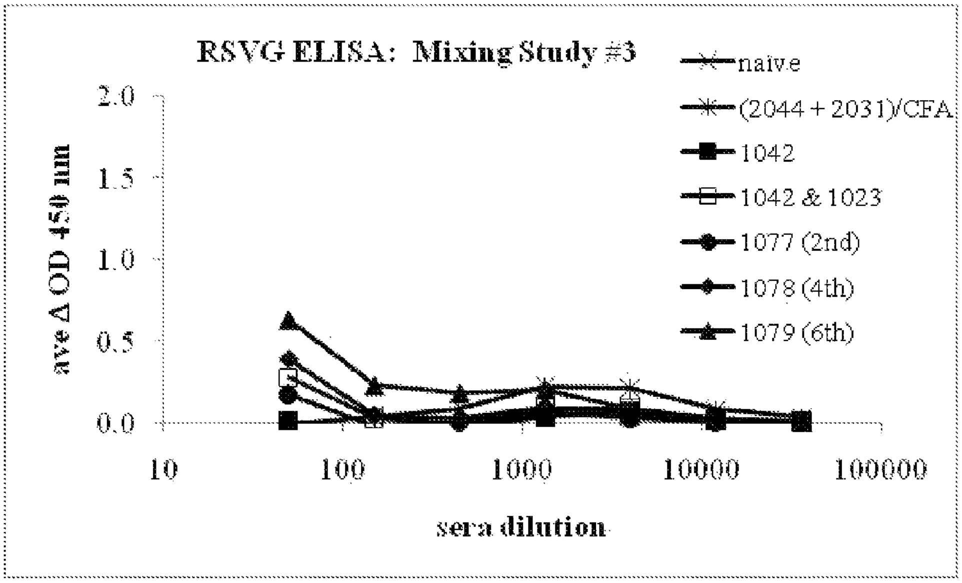
FIGS. 14 and 15 show the antibody response after prime (14) and boost (15) after RSV particle immunization using single epitope and multiple epitope constructs.
Figure 15:
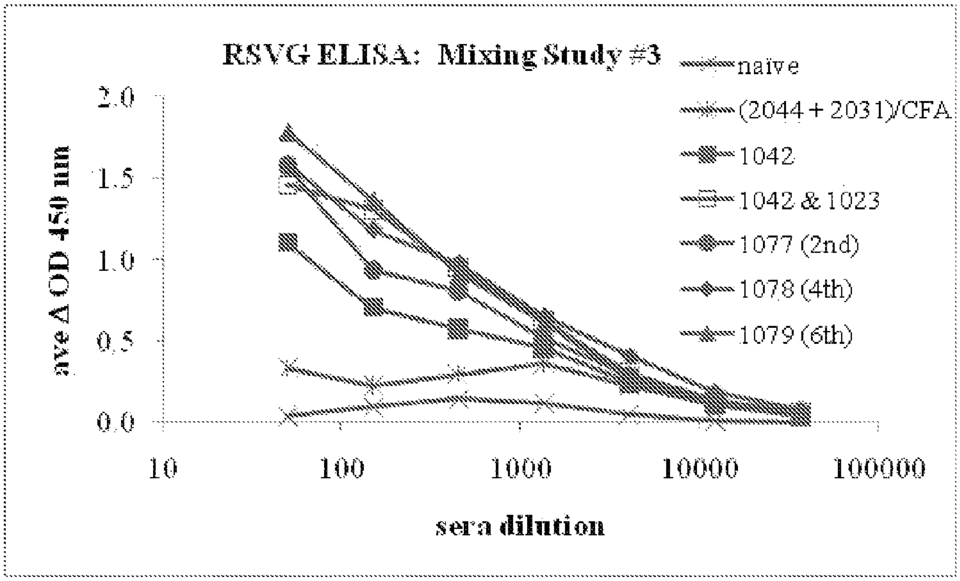
Figure 16:
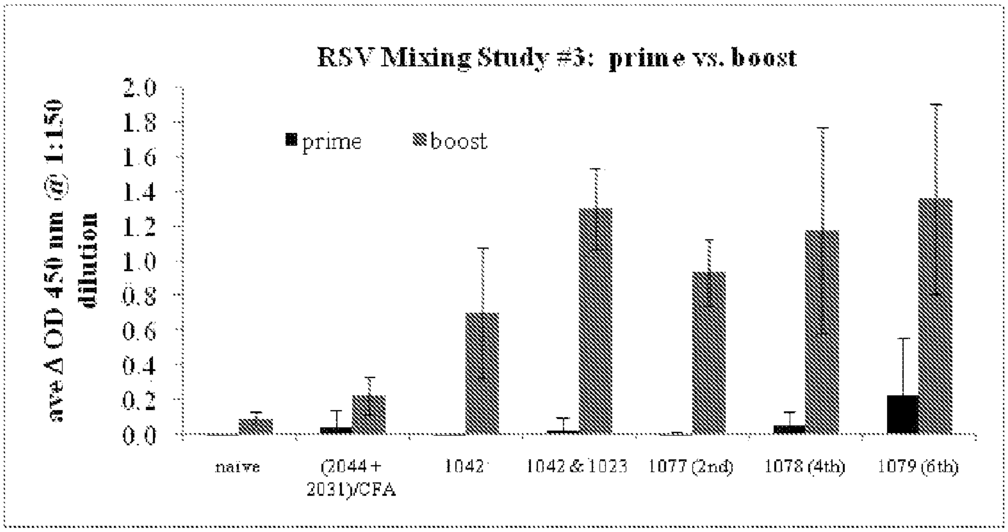
FIG. 16 is a bar graph of the results shown in FIGS. 14 and 15.

The data are shown in FIGS. 14-16.

Example 15

Thiolation of Poly-L-Glutamic Acid (PGA-SH) and Attachment of Cysteine Containing Peptide 32 mg of medium molecular weight PGA sodium salt (sold by Sigma) was dissolved in 1.0 mL of 0.1 M sodium phosphate pH 7.2 buffer. 22 mg of 1-ethyl-3-(3-dimethyl-aminopropyl) carbodiimide (EDC) and 15 mg of sulfo-NHS were added and the solution kept at room temp for 15 min 4.6 mg of cystamine HCl salt was added and the solution was allowed to react for 90 min. The product was purified by passage over a Desalt® column (sold by Pierce) prequilibrated with dilute acetate buffer at pH 4.5. The eluent was frozen and stored at −80° C. The extent of thiolation was estimated by Ellman's (DTNB) assay and was found to be approximately 24% of total glutamate residues.

A synthetic peptide containing a known T-cell epitope from the RSV G protein (RSV G residues 186-198, SED ID NO: 24 CKRIPNKKPGKKT) can be readily synthesized by standard solid phase peptide synthesis methods. 15 mg of PGA-SH in 0.5 mL phosphate buffer pH 7 can be treated with 0.4 mg DTNB (~1.0 umol) for 30 min at room temperature. The solution will turn yellow. The activation reaction can be monitored by UV spectroscopy and judged complete when there is no more increase in absorbance as 412 nm. 1.5 mg cysteine containing epitope peptide (~1 umol) can then be added and the solution allowed to react for 10 min. The product can be partially purified by dialysis using 5000 MW cut off dialysis tubing and the peptide loading can be confirmed by amino acid analysis.

Example 16

Thioether Attachment of an Epitope Peptide to PGA-SH

A synthetic peptide containing a known T-cell epitope from the RSV G protein (RSV G residues 187-198, SEQ ID NO: 25 KRIPNKKPGKKT) can be synthesized on a solid phase peptide synthesis resin. Prior to resin cleavage, a bromoacetyl group can be installed at the N-terminal by treating the resin with bromoacetic anhydride. Following resin cleavage and purification 1.5 mg (~1 umol) of the peptide (bromoacetyl-KRIPNKKPGKKT) can be added to a solution of 15 mg PGA-SH in phosphate buffer pH 7. The product can be partially purified by dialysis using 5000 MW cut off dialysis tubing and the peptide loading can be confirmed by amino acid analysis.

Example 17

Cross Linking of a Cysteine Containing Epitope Peptide to PLL

A stock solution of medium MW PLL (sold by Sigma) at a convenient concentration, typically 0.5-50 mg/mL, and at near neutral pH, typically pH 6-8, is mixed with a cross linker such as sulfosuccinimidyl 4-[N-maleimidomethyl] cyclohexane-1-carboxylate (sulfo-SMCC). The amount of sulfo-SMCC can vary but sufficient amount is used to modify between 1-25% of the lysine residues in the PLL. Typical reaction time is 0.5-5 hours. Excess sulfo-SMCC reagent is then removed by either passing the reaction solution over a gel filtration column or by dialysis. The modified PLL is then allowed to react with a slight excess of cysteine containing epitope peptide at near neutral pH, typically pH 6-8. The final PLL-epitope conjugate is purified by either passing the solution over a gel filtration column or by dialysis. This reagent will be suitable for incorporation into a polyelectrolyte ELBL film by methods similarly used for PLL.

Example 18

Figure 17:
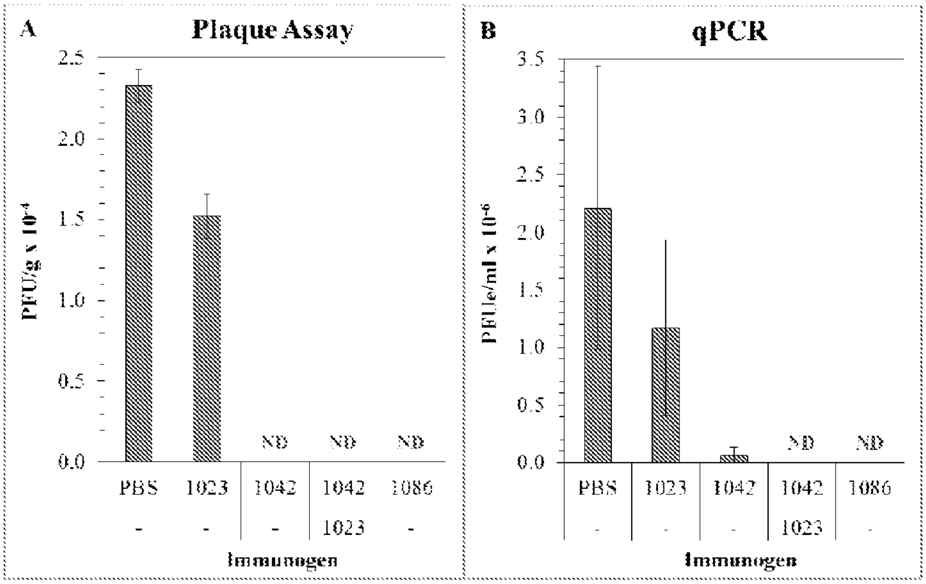
FIG. 17 shows the results of a challenge with live RSV of mice immunized with RSV nanoparticles containing either an RSV-G, RSV-M2 or a combination. Data are shown as a plaque assay and a qPCR assay.

Protection from RSV Challenge Following Immunization of Mice with Nanoparticles Mice were challenged intranasally with RSV on day 28, and sacrificed 5 days later. Lungs were harvested and homogenized, and viral titers were measured by Vero cell assay and by qPCR amplification of the RSV-M gene. The results (FIG. 17) demonstrate essentially complete protection with any formulation that contains RSV-G (groups 3-6). In this study, RSV-M2 alone did not protect, nor did the multivalent vaccine work better than the RSV-G alone, possibly because of the relatively high dose used (10 μg).

Example 19

Figure 18:
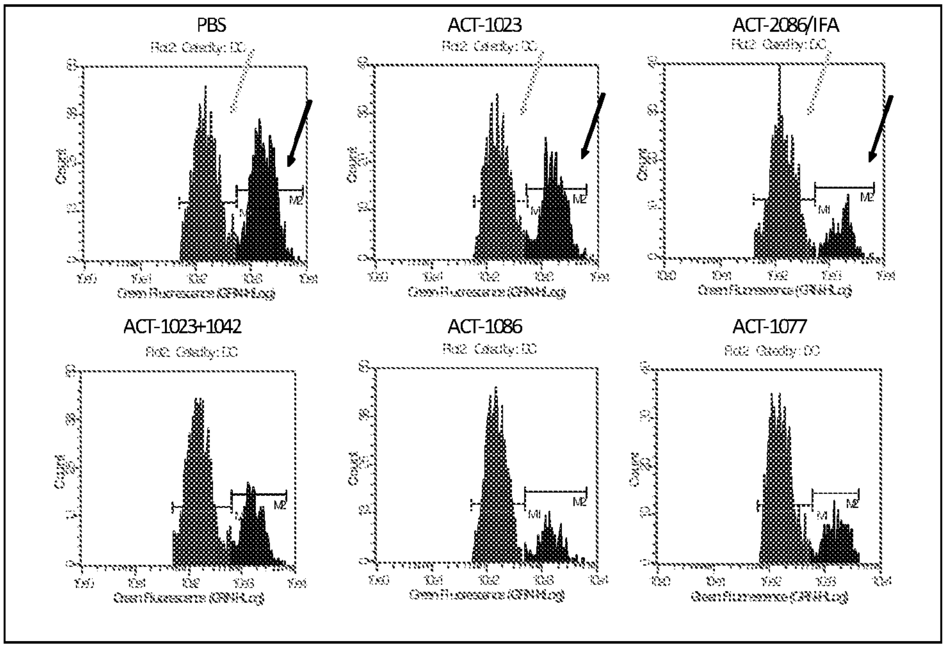
FIG. 18: Induction of in vivo CTL activity by RSV nanoparticle immunization. BALB/c mice were immunized as shown and challenged 7 days later by i.v. injection of syngeneic spleen cells pulsed with ACT-2031 (RSV-M2; SEQ ID NO: 12) and labeled with a high dose of fluorescent tracer CFSE (rightmost peak in each panel) mixed with syngeneic spleen cells labeled with a low dose of CFSE and no target peptide (leftmost peak in each panel). The next day, spleens of the immunzied mice were analyzed by flow cytometry to detect survival of the differentially-labeled donor target cells. Each histogram shows the results from a single immunized mouse in that treatment group.
Figure 19:
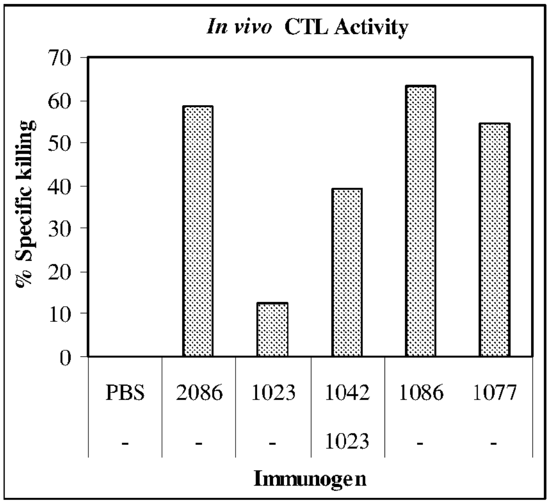
FIG. 19: Induction of in vivo CTL activity by RSV nanoparticle immunization. Results show percent specific killing of RSV-M2-labeled target cells in FIG. 18 calculated by comparing the relative number of cells in each peak within a histogram.

Immunogenicity of Multivalent Nanoparticles Containing RSV-G and RSV-M2 Epitopes on the Same or Different Layers Mice were immunized on day 0 by injection of RSV nanoparticle constructs into the rear footpad; immunogens included ACT-1023 (RSV-M2), ACT-1042 (RSV-G)+ACT-1023 (RSV-M2), ACT-1086 (RSV-M2+G fusion peptide in a single layer) and ACT-1077 (RSV-G+RSV-M2 peptides in different layers). Mice were challenged with RSV-M2-loaded, CFSE-labeled target cells on day 7. The next day, spleen cells were analyzed by flow cytometry to detect survival of the CFSE-labeled target cells. The results (FIGS. 18 and 19) show that while immunization with any nanoparticle containing RSV-M2 epitope elicited RSV-M2-specific effector cells, the response was more potent in mice immunized with multivalent (RSV-M2+G) constructs than in mice immunized with monovalent (RSV-M2) constructs.

Figure 20:
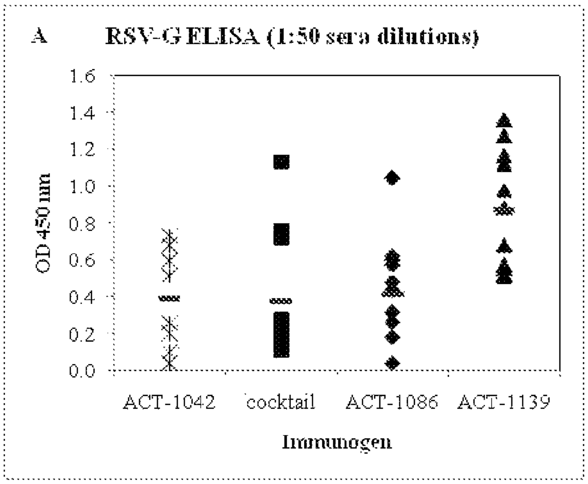
FIGS. 20 and 21: RSV-G-specific antibody responses. BALB/c mice were immunized on days 0 and 21. RSV-G-specific IgG antibody titers in post-boost sera were measured by ELISA. (20) OD values of individual sera at 1:50 dilution. cocktail=ACT-1023+1042. The horizontal bars represent the average of the individual values within a group. (21) Average of 5 sera per group in serial titrations.
Figure 21:
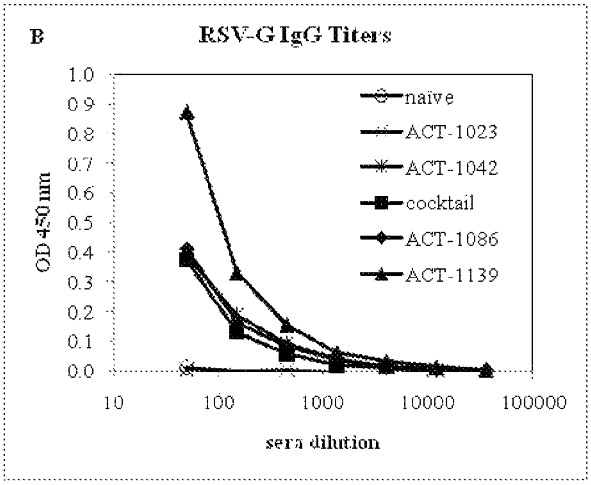

In a separate study, mice were immunized on days 0 and 21 by injection of RSV nanoparticle constructs into the rear footpad; immunogens included ACT-1023 (RSV-M2), ACT-1042 (RSV-G), ACT-1042+ACT-1023, ACT-1086 (RSV-M2+G fusion peptide in a single layer) and ACT-1139 (RSV-G+RSV-M2 peptides co-loaded in the same layer). Mice were bled on day 28 and the sera were analyzed for RSV-G-specific antibodies by ELISA. The results (FIG. 20, 21) show that all formulations which contained the RSV-G epitope elicited antibody titers, while the ACT-1139 multivalent nanoparticle appeared to be the most potent.

The use of the terms "a" and "an" and "the" and similar referents (especially in the context of the following claims) are to be construed to cover both the singular and the plural, unless otherwise indicated herein or clearly contradicted by context. The terms first, second, etc., as used herein are not meant to denote any particular ordering, but simply for convenience to denote a plurality of, for example, layers. The terms "comprising", "having", "including", and "containing" are to be construed as open-ended terms (i.e., meaning "including, but not limited to") unless otherwise noted. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the invention as used herein.

While the invention has been described with reference to an exemplary embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims. Any combination of the above-described elements in all possible variations thereof is encompassed by the invention unless otherwise indicated herein or otherwise clearly contradicted by context.

The invention claimed is:

1. A composition comprising particles containing RSV epitopes, the particles comprising an RSV-M2 peptide epitope and an RSV-G peptide epitope, wherein the RSV-M2 and RSV-G peptide epitopes are covalently linked to one or more surface adsorption regions, or are covalently linked to a same surface adsorption region, to form one or more designed polypeptides, wherein the one or more designed polypeptides are in one or more layers of the same multilayer film, wherein the RSV-M2 peptide epitope includes RSV-$M2_{81-95}$ and the RSV-G peptide epitope includes RSV-$G_{169-191}$, wherein the one or more designed polypeptides does not include full-length RSV-M2 or full-length RSV-G, and wherein surface adsorption regions contain at least eight amino acid residues and have the same sign of charge as the designed polypeptide;

wherein the multilayer film comprises two or more layers of polyelectrolytes, wherein adjacent layers comprise oppositely charged polyelectrolytes, and wherein the polyelectrolye comprises a polycationic material or a polyanionic material having a molecular weight of greater than 1,000 and at least 5 charges per molecule, and wherein the multilayer film is deposited on a core particle or forms a hollow particle to provide the composition comprising particles containing the RSV-M2 and RSV-G peptide epitopes.

2. The composition of claim 1, wherein the designed polypeptide is at least 15 amino acids long and has a net charge per residue at neutral pH of greater than or equal to 0.1.

3. The composition of claim 1, wherein the RSV-M2 peptide epitope and the RSV-G peptide epitope are present in a single polypeptide.

4. The composition of claim 1, wherein the RSV-M2 peptide epitope and the RSV-G peptide epitope are present in distinct polypeptides.

5. The composition of claim 1, wherein the RSV-M2 peptide epitope elicits a specific cytotoxic or helper T-cell response and RSV-G peptide epitope elicits a specific antibody response.

6. The composition of claim 5, wherein the RSV-M2 peptide epitope comprises SEQ ID NO: 4.

7. The composition of claim 1, wherein two or more of the layers of the multilayer film are covalently cross linked.

8. The composition of claim 7, wherein two or more of the layers of the multilayer film are covalently cross linked by amide bonds.

9. The composition of claim 7, wherein two or more of the layers of the multilayer film are covalently cross linked by disulfide bonds.

* * * * *

UNITED STATES PATENT AND TRADEMARK OFFICE

CERTIFICATE OF CORRECTION

PATENT NO. : 9,487,593 B2
APPLICATION NO. : 13/177671
DATED : November 8, 2016
INVENTOR(S) : Thomas J. Powell and James Gorham Boyd It is certified that error appears in the above-identified patent and that said Letters Patent is hereby corrected as shown below:

In the Specification

Column 1 at Line 12, insert:

--STATEMENT REGARDING FEDERALLY SPONSORED RESEARCH & DEVELOPMENT
This invention was made with government support under AI088744 awarded by the National Institutes of Health. The government has certain rights in the invention.--

Signed and Sealed this
Twenty-fourth Day of April, 2018

Andrei Iancu
*Director of the United States Patent and Trademark Office*

SEQUENCE LISTING

```
<160> NUMBER OF SEQ ID NOS: 25

<210> SEQ ID NO 1
<211> LENGTH: 298
<212> TYPE: PRT
<213> ORGANISM: respiratory syncytial virus

<400> SEQUENCE: 1

Met Ser Lys Asn Lys Asp Gln Arg Thr Ala Lys Thr Leu Glu Arg Thr
1               5                   10                  15

Trp Asp Thr Leu Asn His Leu Leu Phe Ile Ser Ser Cys Leu Tyr Lys
            20                  25                  30

Leu Asn Leu Lys Ser Val Ala Gln Ile Thr Leu Ser Ile Leu Ala Met
        35                  40                  45

Ile Ile Ser Thr Ser Leu Ile Ile Ala Ala Ile Ile Phe Ile Ala Ser
    50                  55                  60

Ala Asn His Lys Val Thr Pro Thr Thr Ala Ile Ile Gln Asp Ala Thr
65                  70                  75                  80

Ser Gln Ile Lys Asn Thr Thr Pro Thr Tyr Leu Thr Gln Asn Pro Gln
                85                  90                  95

Leu Gly Ile Ser Pro Ser Asn Pro Ser Glu Ile Thr Ser Gln Ile Thr
            100                 105                 110

Thr Ile Leu Ala Ser Thr Thr Pro Gly Val Lys Ser Thr Leu Gln Ser
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Ser Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
            180                 185                 190
```

-continued

Lys Pro Gly Lys Lys Thr Thr Thr Lys Pro Thr Lys Lys Pro Thr Leu
195 200 205

Lys Thr Thr Lys Lys Asp Pro Lys Pro Gln Thr Thr Lys Ser Lys Glu
210 215 220

Val Pro Thr Thr Lys Pro Thr Glu Glu Pro Thr Ile Asn Thr Thr Lys
225 230 235 240

Thr Asn Ile Ile Thr Thr Leu Leu Thr Ser Asn Thr Thr Gly Asn Pro
245 250 255

Glu Leu Thr Ser Gln Met Glu Thr Phe His Ser Thr Ser Ser Glu Gly
260 265 270

Asn Pro Ser Pro Ser Gln Val Ser Thr Thr Ser Glu Tyr Pro Ser Gln
275 280 285

Pro Ser Ser Pro Pro Asn Thr Pro Arg Gln
290 295

<210> SEQ ID NO 2
<211> LENGTH: 574
<212> TYPE: PRT
<213> ORGANISM: respiratory syncytial virus

<400> SEQUENCE: 2

Met Glu Leu Leu Ile Leu Lys Ala Asn Ala Ile Thr Thr Ile Leu Thr
1 5 10 15

Ala Val Thr Phe Cys Phe Ala Ser Gly Gln Asn Ile Thr Glu Glu Phe
20 25 30

Tyr Gln Ser Thr Cys Ser Ala Val Ser Lys Gly Tyr Leu Ser Ala Leu
35 40 45

Arg Thr Gly Trp Tyr Thr Ser Val Ile Thr Ile Glu Leu Ser Asn Ile
50 55 60

Lys Glu Asn Lys Cys Asn Gly Thr Asp Ala Lys Val Lys Leu Ile Lys
65 70 75 80

Gln Glu Leu Asp Lys Tyr Lys Asn Ala Val Thr Glu Leu Gln Leu Leu
85 90 95

Met Gln Ser Thr Pro Pro Thr Asn Asn Arg Ala Arg Arg Glu Leu Pro
100 105 110

Arg Phe Met Asn Tyr Thr Leu Asn Asn Ala Lys Lys Thr Asn Val Thr
115 120 125

Leu Ser Lys Lys Arg Lys Arg Arg Phe Leu Gly Phe Leu Leu Gly Val
130 135 140

Gly Ser Ala Ile Ala Ser Gly Val Ala Val Ser Lys Val Leu His Leu
145 150 155 160

Glu Gly Glu Val Asn Lys Ile Lys Ser Ala Leu Leu Ser Thr Asn Lys
165 170 175

Ala Val Val Ser Leu Ser Asn Gly Val Ser Val Leu Thr Ser Lys Val
180 185 190

Leu Asp Leu Lys Asn Tyr Ile Asp Lys Gln Leu Leu Pro Ile Val Asn
195 200 205

Lys Gln Ser Cys Ser Ile Ser Asn Ile Glu Thr Val Ile Glu Phe Gln
210 215 220

Gln Lys Asn Asn Arg Leu Leu Glu Ile Thr Arg Glu Phe Ser Val Asn
225 230 235 240

Ala Gly Val Thr Thr Pro Val Ser Thr Tyr Met Leu Thr Asn Ser Glu
245 250 255

Leu Leu Ser Leu Ile Asn Asp Met Pro Ile Thr Asn Asp Gln Lys Lys

-continued

```
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Ile Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Met Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Thr Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570


<210> SEQ ID NO 3
<211> LENGTH: 192
<212> TYPE: PRT
<213> ORGANISM: respiratory syncytial virus

<400> SEQUENCE: 3

Met Ser Arg Arg Asn Pro Cys Lys Phe Glu Ile Arg Gly His Cys Leu
1               5                   10                  15

Asn Gly Lys Arg Cys His Phe Ser His Asn Tyr Phe Glu Trp Pro Pro
            20                  25                  30

His Ala Leu Leu Val Arg Gln Asn Phe Met Leu Asn Arg Ile Leu Lys
        35                  40                  45

Ser Met Asp Lys Ser Ile Asp Thr Leu Ser Glu Ile Ser Gly Ala Ala
    50                  55                  60
```

-continued

```
Glu Leu Asp Arg Thr Glu Glu Tyr Ala Leu Gly Val Val Gly Val Leu
65                  70                  75                  80

Glu Ser Tyr Ile Gly Ser Ile Asn Asn Ile Thr Lys Gln Ser Ala Cys
                85                  90                  95

Val Ala Met Ser Lys Leu Leu Thr Glu Leu Asn Ser Asp Asp Ile Lys
            100                 105                 110

Lys Leu Arg Asp Asn Glu Glu Leu Asn Ser Pro Lys Ile Arg Val Tyr
        115                 120                 125

Asn Thr Val Ile Ser Tyr Ile Glu Ser Asn Arg Lys Asn Asn Lys Gln
    130                 135                 140

Thr Ile His Leu Leu Lys Arg Leu Pro Ala Asp Val Leu Lys Lys Thr
145                 150                 155                 160

Ile Lys Asn Thr Leu Asp Ile His Lys Ser Ile Thr Ile Asn Asn Pro
                165                 170                 175

Lys Glu Ser Thr Asp Thr Asn Asp His Ala Lys Asn Asn Asp Thr Thr
            180                 185                 190


<210> SEQ ID NO 4
<211> LENGTH: 29
<212> TYPE: PRT
<213> ORGANISM: respiratory syncytial virus

<400> SEQUENCE: 4

His Phe Glu Val Phe Asn Phe Val Pro Cys Ser Ile Cys Ser Asn Asn
1               5                   10                  15

Pro Thr Cys Trp Ala Ile Cys Lys Arg Ile Pro Asn Lys
            20                  25


<210> SEQ ID NO 5
<211> LENGTH: 15
<212> TYPE: PRT
<213> ORGANISM: respiratory syncytial virus

<400> SEQUENCE: 5

Gly Trp Tyr Thr Ser Val Ile Thr Ile Glu Leu Ser Asn Ile Lys
1               5                   10                  15


<210> SEQ ID NO 6
<211> LENGTH: 16
<212> TYPE: PRT
<213> ORGANISM: respiratory syncytial virus

<400> SEQUENCE: 6

Asp Arg Gly Trp Tyr Ser Asp Asn Ala Gly Ser Val Ser Phe Phe Arg
1               5                   10                  15


<210> SEQ ID NO 7
<211> LENGTH: 15
<212> TYPE: PRT
<213> ORGANISM: Artificial Sequence
<220> FEATURE:
<223> OTHER INFORMATION: CD8+ T-cell target shown to modulate Th2
      responses to RSV-G

<400> SEQUENCE: 7

Glu Ser Tyr Ile Gly Ser Ile Asn Asn Ile Thr Lys Gln Ser Ala
1               5                   10                  15


<210> SEQ ID NO 8
<211> LENGTH: 50
<212> TYPE: PRT
<213> ORGANISM: Artificial Sequence
```

```
<220> FEATURE:
<223> OTHER INFORMATION: RSV-G164-191K21Y amide

<400> SEQUENCE: 8

His Phe Glu Val Phe Asn Phe Val Pro Cys Ser Ile Cys Ser Asn Asn
1               5                   10                  15

Pro Thr Cys Trp Ala Ile Cys Lys Arg Ile Pro Asn Lys Lys Lys Lys
            20                  25                  30

Lys Lys Lys Lys Lys Lys Lys Lys Lys Lys Lys Lys Lys Lys Lys Lys
        35                  40                  45

Lys Tyr
    50


<210> SEQ ID NO 9
<211> LENGTH: 50
<212> TYPE: PRT
<213> ORGANISM: Artificial Sequence
<220> FEATURE:
<223> OTHER INFORMATION: RSV-G164-191K21Y amide with capped cysteine
      residues
<220> FEATURE:
<221> NAME/KEY: MOD_RES
<222> LOCATION: (10)..(10)
<223> OTHER INFORMATION: Xaa is carboxamidomethylcysteine
<220> FEATURE:
<221> NAME/KEY: MOD_RES
<222> LOCATION: (13)..(13)
<223> OTHER INFORMATION: Xaa is carboxamidomethylcysteine
<220> FEATURE:
<221> NAME/KEY: MOD_RES
<222> LOCATION: (19)..(19)
<223> OTHER INFORMATION: Xaa is carboxamidomethylcysteine
<220> FEATURE:
<221> NAME/KEY: MOD_RES
<222> LOCATION: (23)..(23)
<223> OTHER INFORMATION: Xaa is carboxamidomethylcysteine

<400> SEQUENCE: 9

His Phe Glu Val Phe Asn Phe Val Pro Xaa Ser Ile Xaa Ser Asn Asn
1               5                   10                  15

Pro Thr Xaa Trp Ala Ile Xaa Lys Arg Ile Pro Asn Lys Lys Lys Lys
            20                  25                  30

Lys Lys Lys Lys Lys Lys Lys Lys Lys Lys Lys Lys Lys Lys Lys Lys
        35                  40                  45

Lys Tyr
    50


<210> SEQ ID NO 10
<211> LENGTH: 10
<212> TYPE: PRT
<213> ORGANISM: Artificial Sequence
<220> FEATURE:
<223> OTHER INFORMATION: cyclo-RSV-G175-184

<400> SEQUENCE: 10

Ile Cys Ser Asn Asn Pro Thr Cys Trp Ala
1               5                   10


<210> SEQ ID NO 11
<211> LENGTH: 45
<212> TYPE: PRT
<213> ORGANISM: Artificial Sequence
<220> FEATURE:
<223> OTHER INFORMATION: RSV-G169-191K21Y

<400> SEQUENCE: 11
```

```
Asn Phe Val Pro Cys Ser Ile Cys Ser Asn Asn Pro Thr Cys Trp Ala
1               5                   10                  15

Ile Cys Lys Arg Ile Pro Asn Lys Lys Lys Lys Lys Lys Lys Lys Lys
            20                  25                  30

Lys Lys Lys Lys Lys Lys Lys Lys Lys Lys Lys Lys Tyr
        35                  40                  45


<210> SEQ ID NO 12
<211> LENGTH: 34
<212> TYPE: PRT
<213> ORGANISM: Artificial Sequence
<220> FEATURE:
<223> OTHER INFORMATION: RSV-M281-98 (KVKA)4 amide

<400> SEQUENCE: 12

Glu Ser Tyr Ile Gly Ser Ile Asn Asn Ile Thr Lys Gln Ser Ala Ser
1               5                   10                  15

Val Ala Lys Val Lys Ala Lys Val Lys Ala Lys Val Lys Ala Lys Val
            20                  25                  30

Lys Ala


<210> SEQ ID NO 13
<211> LENGTH: 67
<212> TYPE: PRT
<213> ORGANISM: Artificial Sequence
<220> FEATURE:
<223> OTHER INFORMATION: RSV-M281-98G164-191 K20Y amide

<400> SEQUENCE: 13

Glu Ser Tyr Ile Gly Ser Ile Asn Asn Ile Thr Lys Gln Ser Ala Ser
1               5                   10                  15

Gly Ser His Phe Glu Val Phe Asn Phe Val Pro Cys Ser Ile Cys Ser
            20                  25                  30

Asn Asn Pro Thr Cys Trp Ala Ile Cys Lys Arg Ile Pro Asn Lys Lys
        35                  40                  45

Lys Lys Lys Lys Lys Lys Lys Lys Lys Lys Lys Lys Lys Lys Lys Lys
    50                  55                  60

Lys Lys Tyr
65


<210> SEQ ID NO 14
<211> LENGTH: 51
<212> TYPE: PRT
<213> ORGANISM: Artificial Sequence
<220> FEATURE:
<223> OTHER INFORMATION: RSV-G169-198 K20Y amide

<400> SEQUENCE: 14

Asn Phe Val Pro Cys Ser Ile Cys Ser Asn Asn Pro Thr Cys Trp Ala
1               5                   10                  15

Ile Cys Lys Arg Ile Pro Asn Lys Lys Pro Gly Lys Lys Thr Lys Lys
            20                  25                  30

Lys Lys Lys Lys Lys Lys Lys Lys Lys Lys Lys Lys Lys Lys Lys Lys
        35                  40                  45

Lys Lys Tyr
    50


<210> SEQ ID NO 15
<211> LENGTH: 56
<212> TYPE: PRT
<213> ORGANISM: Artificial Sequence
```

<220> FEATURE:
<223> OTHER INFORMATION: RSV-G164-198 K20Y amide

<400> SEQUENCE: 15

His Phe Glu Val Phe Asn Phe Val Pro Cys Ser Ile Cys Ser Asn Asn
1               5                   10                  15

Pro Thr Cys Trp Ala Ile Cys Lys Arg Ile Pro Asn Lys Lys Pro Gly
            20                  25                  30

Lys Lys Thr Lys Lys Lys Lys Lys Lys Lys Lys Lys Lys Lys Lys Lys
        35                  40                  45

Lys Lys Lys Lys Lys Lys Lys Tyr
    50                  55

<210> SEQ ID NO 16
<211> LENGTH: 39
<212> TYPE: PRT
<213> ORGANISM: Artificial Sequence
<220> FEATURE:
<223> OTHER INFORMATION: RSV M2 81-98 K20Y amide

<400> SEQUENCE: 16

Glu Ser Tyr Ile Gly Ser Ile Asn Asn Ile Thr Lys Gln Ser Ala Ser
1               5                   10                  15

Val Ala Lys Lys Lys Lys Lys Lys Lys Lys Lys Lys Lys Lys Lys Lys
            20                  25                  30

Lys Lys Lys Lys Lys Lys Tyr
        35

<210> SEQ ID NO 17
<211> LENGTH: 21
<212> TYPE: PRT
<213> ORGANISM: Artificial Sequence
<220> FEATURE:
<223> OTHER INFORMATION: K20Y tail

<400> SEQUENCE: 17

Lys Lys Lys Lys Lys Lys Lys Lys Lys Lys Lys Lys Lys Lys Lys Lys
1               5                   10                  15

Lys Lys Lys Lys Tyr
            20

<210> SEQ ID NO 18
<211> LENGTH: 23
<212> TYPE: PRT
<213> ORGANISM: Artificial Sequence
<220> FEATURE:
<223> OTHER INFORMATION: G protein sequence

<400> SEQUENCE: 18

Asn Phe Val Pro Cys Ser Ile Cys Ser Asn Asn Pro Thr Cys Trp Ala
1               5                   10                  15

Ile Cys Lys Arg Ile Pro Asn
            20

<210> SEQ ID NO 19
<211> LENGTH: 22
<212> TYPE: PRT
<213> ORGANISM: Artificial Sequence
<220> FEATURE:
<223> OTHER INFORMATION: K21Y tail

<400> SEQUENCE: 19

Lys Lys Lys Lys Lys Lys Lys Lys Lys Lys Lys Lys Lys Lys Lys Lys

-continued

```
1               5                   10                  15

Lys Lys Lys Lys Lys Tyr
            20


<210> SEQ ID NO 20
<211> LENGTH: 28
<212> TYPE: PRT
<213> ORGANISM: Artificial Sequence
<220> FEATURE:
<223> OTHER INFORMATION: G protein sequence

<400> SEQUENCE: 20

His Phe Glu Val Phe Asn Phe Val Pro Cys Ser Ile Cys Ser Asn Asn
1               5                   10                  15

Pro Thr Cys Trp Ala Ile Cys Lys Arg Ile Pro Asn
            20                  25


<210> SEQ ID NO 21
<211> LENGTH: 28
<212> TYPE: PRT
<213> ORGANISM: Artificial Sequence
<220> FEATURE:
<223> OTHER INFORMATION: G protein sequence

<400> SEQUENCE: 21

His Phe Glu Val Phe Asn Phe Val Pro Cys Ser Ile Cys Ser Asn Asn
1               5                   10                  15

Pro Thr Cys Trp Ala Ile Cys Lys Arg Ile Pro Asn
            20                  25


<210> SEQ ID NO 22
<211> LENGTH: 30
<212> TYPE: PRT
<213> ORGANISM: Artificial Sequence
<220> FEATURE:
<223> OTHER INFORMATION: G protein sequence

<400> SEQUENCE: 22

Asn Phe Val Pro Cys Ser Ile Cys Ser Asn Asn Pro Thr Cys Trp Ala
1               5                   10                  15

Ile Cys Lys Arg Ile Pro Asn Lys Lys Pro Gly Lys Lys Thr
            20                  25                  30


<210> SEQ ID NO 23
<211> LENGTH: 34
<212> TYPE: PRT
<213> ORGANISM: Artificial Sequence
<220> FEATURE:
<223> OTHER INFORMATION: G protein sequence

<400> SEQUENCE: 23

His Phe Glu Val Phe Asn Phe Val Pro Cys Ser Ile Cys Ser Asn Asn
1               5                   10                  15

Pro Thr Cys Trp Ala Ile Cys Lys Arg Ile Pro Asn Lys Lys Pro Gly
            20                  25                  30

Lys Lys


<210> SEQ ID NO 24
<211> LENGTH: 13
<212> TYPE: PRT
<213> ORGANISM: Artificial Sequence
<220> FEATURE:
<223> OTHER INFORMATION: RSV G residues 186-198
```

-continued

```
<400> SEQUENCE: 24

Cys Lys Arg Ile Pro Asn Lys Lys Pro Gly Lys Lys Thr
1               5                   10


<210> SEQ ID NO 25
<211> LENGTH: 12
<212> TYPE: PRT
<213> ORGANISM: Artificial Sequence
<220> FEATURE:
<223> OTHER INFORMATION: RSV G residues 187-198

<400> SEQUENCE: 25

Lys Arg Ile Pro Asn Lys Lys Pro Gly Lys Lys Thr
1               5                   10
```